(12) United States Patent
Gonzales et al.

(10) Patent No.: US 12,167,912 B2
(45) Date of Patent: Dec. 17, 2024

(54) IMPACT SENSING WEARABLE DEVICE AND METHOD

(71) Applicant: Force Impact Technologies, Inc., Gilbert, AZ (US)

(72) Inventors: Anthony M. Gonzales, Canoga Park, CA (US); Robert Merriman, Gilbert, AZ (US)

(73) Assignee: FORCE IMPACT TECHNOLOGIES INC., Gilbert, AZ (US)

( * ) Notice: Subject to any disclaimer, the term of this patent is extended or adjusted under 35 U.S.C. 154(b) by 0 days.

(21) Appl. No.: 18/339,040

(22) Filed: Jun. 21, 2023

(65) Prior Publication Data

US 2023/0346263 A1 Nov. 2, 2023

Related U.S. Application Data

(63) Continuation of application No. 18/337,888, filed on Jun. 20, 2023, which is a continuation of application
(Continued)

(51) Int. Cl.
*A61B 5/11* (2006.01)
*A61B 5/00* (2006.01)
(Continued)

(52) U.S. Cl.
CPC ............ *A61B 5/1122* (2013.01); *A61B 5/002* (2013.01); *A61B 5/0022* (2013.01); *A61B 5/11* (2013.01);
(Continued)

(58) Field of Classification Search
CPC .............. A63B 71/085; A63B 2220/53; A63B 2220/40; A63B 2220/44; A42B 3/046;
(Continued)

(56) References Cited

U.S. PATENT DOCUMENTS 4,672,959 A 6/1987 May
4,765,234 A 8/1988 Lake, Jr.
(Continued)

FOREIGN PATENT DOCUMENTS

CA 2 816 982 5/2012
CN 201505230 6/2010
(Continued)

OTHER PUBLICATIONS

Greenwald, R. M. et al., "Head Impact Severity Measures for Evaluating Mild Traumatic Brain Injury Risk Exposure," Neurosurgery 62(4):789-798, Apr. 2008.
(Continued)

*Primary Examiner* — Yi-Shan Yan
*Assistant Examiner* — Jonathan E. Cooper
(74) *Attorney, Agent, or Firm* — Nixon Peabody LLP

(57) ABSTRACT

A mouth guard senses concussive forces, calculates risk factors for head injury, and displays status of risk and potential injury. The mouth guard may be used to identify, treat and prevent exacerbating injury. The mouth guard can be programmed with biometric data to better calculate and anticipate impact thresholds and more precisely predict and prevent injury.

11 Claims, 15 Drawing Sheets

Related U.S. Application Data

No. 17/443,019, filed on Jul. 19, 2021, which is a continuation of application No. 15/591,003, filed on May 9, 2017, now Pat. No. 11,064,913, which is a continuation-in-part of application No. 14/063,354, filed on Oct. 25, 2013, now abandoned.

(51) Int. Cl.
  *A63B 71/06* (2006.01)
  *A63B 71/08* (2006.01)
  *G16H 20/30* (2018.01)
  *G16H 50/30* (2018.01)

(52) U.S. Cl.
  CPC ............ *A61B 5/682* (2013.01); *A61B 5/7275* (2013.01); *A61B 5/7282* (2013.01); *A61B 5/7445* (2013.01); *A63B 71/0622* (2013.01); *A63B 71/085* (2013.01); *A61B 2503/10* (2013.01); *A63B 2220/40* (2013.01); *A63B 2220/44* (2013.01); *A63B 2220/53* (2013.01); *A63B 2225/50* (2013.01); *A63B 2225/74* (2020.08); *G16H 20/30* (2018.01); *G16H 50/30* (2018.01)

(58) Field of Classification Search
  CPC ......... A42B 3/30; A42B 3/042; A42B 3/0433; A61B 2503/10; A61B 5/6814; A61B 5/0042
  USPC .................................................. 600/587, 595
  See application file for complete search history.

(56) References Cited

U.S. PATENT DOCUMENTS

| | | |
|---|---|---|
| 4,977,905 A | 12/1990 | Kittleson |
| 4,979,516 A | 12/1990 | Abraham, II |
| 5,031,638 A | 7/1991 | Castaldi |
| 5,203,351 A | 4/1993 | Adell |
| 5,293,880 A | 3/1994 | Levitt |
| 5,732,715 A | 3/1998 | Jacobs |
| 6,092,524 A | 7/2000 | Barnes |
| 6,178,967 B1 | 1/2001 | Barnes |
| 6,299,441 B1 | 10/2001 | Novak |
| 6,584,978 B1 | 7/2003 | Brett |
| 6,941,952 B1 | 9/2005 | Rush, III |
| 7,827,991 B2 | 11/2010 | Maher |
| 7,950,394 B2 | 5/2011 | Elkin |
| 8,235,052 B2 | 8/2012 | Maurello |
| 8,459,267 B2 | 6/2013 | Zimmerman |
| 8,739,599 B2 | 6/2014 | Hennig |
| 8,766,798 B2 | 7/2014 | Howard |
| 8,945,919 B2 | 2/2015 | Mori |
| 8,959,668 B1 | 2/2015 | Ganes |
| 9,005,120 B2 | 4/2015 | Ryan |
| 9,017,069 B2 | 4/2015 | Boyden |
| 9,044,198 B2 | 6/2015 | Benzel |
| 9,060,986 B2 | 6/2015 | Breitenbach |
| 9,070,269 B2 | 6/2015 | Evans |
| 9,149,227 B2 | 10/2015 | Benzel |
| 9,226,707 B2 | 1/2016 | Huang |
| 9,289,176 B2 | 3/2016 | Benzel |
| 9,585,619 B2 | 3/2017 | Benzel |
| 9,597,567 B1 | 3/2017 | Tran |
| 9,849,364 B2 | 12/2017 | Tran |
| 9,955,918 B2 | 5/2018 | Paris |
| 9,968,777 B1 | 5/2018 | Demarest |
| 9,975,033 B2 | 5/2018 | Tran |
| 10,004,515 B2 | 6/2018 | Smith |
| 10,010,694 B2 | 7/2018 | Lin |
| 10,028,679 B2 | 7/2018 | Paris |
| 10,092,814 B2 | 10/2018 | Wright |
| 10,117,010 B2 | 10/2018 | Spector |
| 10,172,555 B2 | 1/2019 | Cam |
| 10,517,525 B2 | 12/2019 | Yoon |
| 11,064,913 B2 | 7/2021 | Gonzales |
| 11,109,808 B2 | 9/2021 | Yoon |
| 11,179,104 B2 | 11/2021 | Gonzales |
| 11,389,113 B2 | 7/2022 | Gonzales |
| 11,432,767 B2 | 9/2022 | Gonzales |
| 11,510,618 B2 | 11/2022 | Gonzales |
| 11,607,171 B2 | 3/2023 | Gonzales |
| 2003/0154990 A1 | 8/2003 | Parker |
| 2004/0112389 A1 | 6/2004 | Abraham |
| 2005/0113654 A1* | 5/2005 | Weber ............... A61B 5/14551 128/903 |
| 2006/0065277 A1 | 3/2006 | Jacobs |
| 2006/0073433 A1 | 4/2006 | Anderson |
| 2007/0061106 A1 | 3/2007 | Vock |
| 2007/0151567 A1 | 7/2007 | Maurello |
| 2008/0060661 A1 | 3/2008 | Mathias |
| 2008/0269579 A1 | 10/2008 | Schiebler |
| 2009/0210032 A1 | 8/2009 | Beiski |
| 2011/0179851 A1 | 7/2011 | Mack |
| 2011/0181419 A1* | 7/2011 | Mack ..................... G01L 1/26 702/41 |
| 2011/0184319 A1* | 7/2011 | Mack ..................... A42B 3/046 600/595 |
| 2011/0184663 A1 | 7/2011 | Mack |
| 2011/0214478 A1* | 9/2011 | Hennig ................. G01M 7/08 73/12.01 |
| 2011/0218455 A1 | 9/2011 | Hennig |
| 2012/0124720 A1* | 5/2012 | Evans .................. A42B 3/046 2/9 |
| 2012/0143526 A1 | 6/2012 | Benzel |
| 2012/0172677 A1 | 7/2012 | Logan |
| 2012/0172679 A1* | 7/2012 | Logan ................. A61B 5/6803 600/301 |
| 2013/0074248 A1* | 3/2013 | Evans .................. G08B 21/02 340/669 |
| 2013/0110415 A1* | 5/2013 | Davis .................. A61B 5/6803 702/41 |
| 2013/0150684 A1* | 6/2013 | Cooner ............... A61B 5/4082 600/595 |
| 2013/0211270 A1* | 8/2013 | St. Laurent ......... A61B 5/682 600/595 |
| 2013/0271602 A1* | 10/2013 | Bentley ................. G06T 7/215 348/143 |
| 2014/0024971 A1 | 1/2014 | Bunn |
| 2014/0052405 A1* | 2/2014 | Wackym ............. A61B 5/6803 702/141 |
| 2014/0187875 A1* | 7/2014 | Paris .................... A61B 5/682 600/595 |
| 2014/0261464 A1 | 9/2014 | Layzell |
| 2014/0312834 A1 | 10/2014 | Tanabe |
| 2014/0335464 A1 | 11/2014 | Boyden |
| 2015/0040669 A1* | 2/2015 | Borkholder ............ G01P 15/14 73/514.35 |
| 2015/0119759 A1 | 4/2015 | Gonzales |
| 2015/0173666 A1 | 6/2015 | Smith |
| 2015/0173856 A1 | 6/2015 | Lowe |
| 2015/0196252 A1* | 7/2015 | Luliano ................ A61B 5/746 600/595 |
| 2015/0238142 A1 | 8/2015 | Djordjevski |
| 2015/0305671 A1 | 10/2015 | Yoon |
| 2016/0022167 A1 | 1/2016 | Simon |
| 2016/0106346 A1* | 4/2016 | Benzel ................ A61B 5/1122 600/595 |
| 2016/0107067 A1 | 4/2016 | Barnes |
| 2016/0158627 A1 | 6/2016 | Layzell |
| 2016/0158628 A1 | 6/2016 | Layzell |
| 2016/0158629 A1 | 6/2016 | Layzell |
| 2016/0236051 A1 | 8/2016 | Esteves |
| 2016/0242692 A1 | 8/2016 | McAuliffe |
| 2017/0020434 A1 | 1/2017 | Walker |
| 2017/0042272 A1 | 2/2017 | Ferguson |
| 2017/0071538 A1 | 3/2017 | Calcano |
| 2017/0095204 A1 | 4/2017 | Stitzel |
| 2017/0146555 A1 | 5/2017 | Wang |
| 2017/0224252 A1 | 8/2017 | Salzar |
| 2017/0238850 A1 | 8/2017 | Gonzales |
| 2017/0266536 A1 | 9/2017 | Sciortino |

(56) References Cited

U.S. PATENT DOCUMENTS

| | | |
|---|---|---|
| 2017/0282451 A1 | 10/2017 | Layzell |
| 2017/0296897 A1 | 10/2017 | Simpson |
| 2017/0345536 A1 | 11/2017 | Letizia |
| 2017/0357241 A1 | 12/2017 | Huang |
| 2018/0021659 A1 | 1/2018 | Layzell |
| 2018/0056167 A1 | 3/2018 | Wisniewski |
| 2018/0070668 A1 | 3/2018 | Stephens |
| 2018/0078843 A1 | 3/2018 | Tran |
| 2018/0154242 A1 | 6/2018 | Austin |
| 2018/0196079 A1 | 7/2018 | Austin |
| 2018/0264347 A1 | 9/2018 | Tran |
| 2018/0275119 A1 | 9/2018 | Podoly |
| 2018/0326291 A1 | 11/2018 | Tran |
| 2019/0105842 A1 | 4/2019 | Dau |
| 2019/0125261 A1 | 5/2019 | Lathrop |
| 2020/0147473 A1 | 5/2020 | Maloney |
| 2020/0345536 A1 | 11/2020 | Letizia |
| 2020/0367821 A1 | 11/2020 | Redshaw |
| 2022/0104768 A1 | 4/2022 | Vegar |

FOREIGN PATENT DOCUMENTS

| | | |
|---|---|---|
| CN | 203468806 | 3/2014 |
| CN | 102599674 | 7/2014 |
| CN | 106110390 | 11/2016 |
| CN | 105030767 | 2/2018 |
| CN | 108124797 | 6/2018 |
| CN | 108613575 | 10/2018 |
| CN | 109011414 | 12/2018 |
| EP | 1 901 749 | 3/2008 |
| EP | 3 064 242 | 9/2016 |
| GB | 2570726 A | 8/2019 |
| GB | 2577939 A | 4/2020 |
| JP | 2000-070292 A | 3/2000 |
| JP | 2012-147280 A | 8/2012 |
| WO | WO 2017/070343 | 4/2017 |
| WO | WO 2017/091708 | 6/2017 |
| WO | WO 2016/168939 | 10/2017 |

OTHER PUBLICATIONS

Rowson, S. et al., "Linear and Angular Head Acceleration Measurements in Collegiate Football," Journal of Biomechanical Engineering, vol. 131, pp. 061016-1 to 061016-7, ASMA. June 20098.

Simma. B. et al., "Mild head injury in pediatrics: algorithms for management in the ED and in young athletes," American Journal of Emergency Medicine 31, pp. 1133-1138, 2013.

Graham, R. et al., "Sports-related concussions in Youth: Improving the Science, Changing the Culture," National Academies of Sciences, 2013.

Walilko, T. J., "Biomechanical Response of the Temporomandibular Join from Impacts in Boxing," Wayne State University, 2004.

Broglio, S. P., "The Biomechanical Properties of Concussions in High School Football," Med Sci Sports Exerc., 42(11):2064-2071, Nov. 2010.

Gurdjian, E. S., J. Trauma, 6(5):600-4, Sep. 1966.

Camarillo, D., "Head contacts in collegiate football measured with an instrumented mouthguard," Br. J. Sports Med., Abstracts from the 4th International Conference on Concussion in Sport, Zurich. 2012, doi: 10.1136/bjsports-2012-092101.33.

Rowson, S. & Duma, S. M., "Development of the star evaluation system for football helmets: Integrating player head impact and risk of concussion," Ann. Biomed. Eng. 39, pp. 2130-2140, 2011.

Rowson, S. & Duma, S. M., "Brain Injury Prediction: Assessing the Combined Probability of Concussion Using Linear and Rotational Head Acceleration," Annals of Biomedical Engineering, 41(5):873-882, May 2013.

Rowson, S. et al., "Rotational Head Kinetics in Football Impacts: An Injury Risk Function for Concussion," Annals of Biomedical Engineering, 40(1):1-13, Jan. 2013.

Camarillo, D. et al., "An Instrumented Mouthguard for Measuring Linear and Angular Head Impact Kinematics in American Football," Annals of Biomedical Engineering, 41(9):1939-1949, Sep. 2013.

Benjamin Watkins Industrial Design, "X2 Impact Mouthguard," Retrieved from internet, <https://www.behance.net/gallery/X2-Impact-DVT2-Mouthguard/2891933/> Oct. 25, 2013.

Viano. "Football Helmet Drop Tests on Different Fields Using an Instrumented Hybrid III Head," Annals of Biomedical Engineering, 40(1):97-105, Jan. 2012.

European Patent Office, Extended European Search Report for Application No. 22174642.3, dated Sep. 9, 2022 (12 pages).

So Adrienne; "This Smart Mouthguard Can Monitor Concussions"; Wired; Mar. 1, 2018; retrieved from https://www.wired.com/stoy/this-smart-mouthguard-can-monitor-concussions/ on Aug. 30, 2022 (3 pages).

International Search Report and Written Opinion in International Application No. PCT/US2019/068021, mailed Jun. 24, 2020 (16 pages).

* cited by examiner

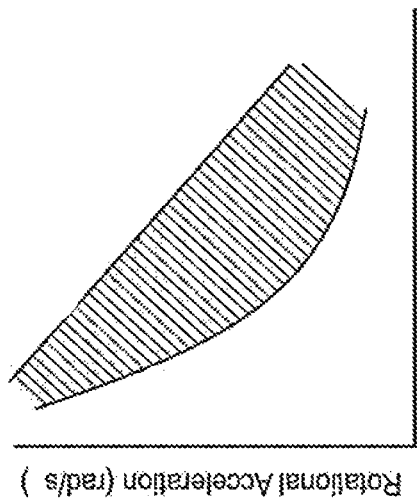
FIG. 12
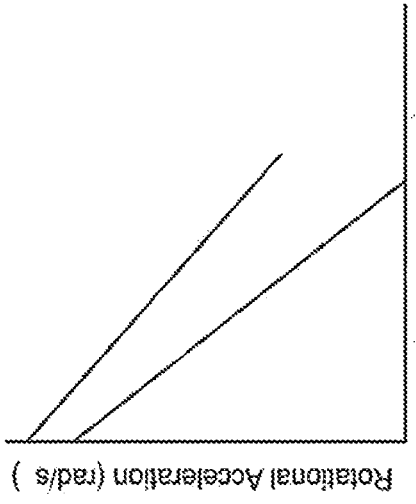
FIG. 14
FIG. 11
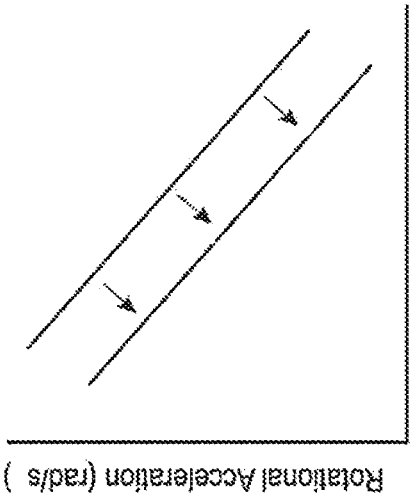
FIG. 13

|  | Adult | | | | Teen | | | | Child | | | |
|---|---|---|---|---|---|---|---|---|---|---|---|---|
|  | Male RED | Male Blue | Female Red | Female Blu | Male Red | Male Blue | Female Re | Female Bl | Male RED | Male Blue | Female Re | Female Bl |
| Below 80lbs | N/A | N/A | N/A | N/A | 24 | 14.4 | 20.4 | 12.2 | 18.0 | 10.8 | 15.3 | 9.2 |
| 81lbs - 106lbs | 40 | 24 | 35 | 21 | 26 | 15.6 | 22.1 | 13.3 | 19.5 | 11.7 | 16.6 | 9.9 |
| 107lbs - 113lbs | 40 | 24 | 38 | 22.8 | 28 | 16.8 | 23.8 | 14.3 | 21.0 | 12.6 | 17.9 | 10.7 |
| 114lbs - 120lbs | 43 | 25.8 | 40 | 24 | 30 | 18 | 25.5 | 15.3 | 22.5 | 13.5 | 19.1 | 11.5 |
| 121lbs - 126lbs | 45 | 27 | 40 | 24 | 30 | 18 | 25.5 | 15.3 | 22.5 | 13.5 | 19.1 | 11.5 |
| 127lbs - 132lbs | 45 | 27 | 40 | 24 | 32 | 19.2 | 27.2 | 16.3 | 24.0 | 14.4 | 20.4 | 12.2 |
| 133lbs - 138lbs | 45 | 27 | 40 | 24 | 32 | 19.2 | 27.2 | 16.3 | 24.0 | 14.4 | 20.4 | 12.2 |
| 139lbs - 145lbs | 50 | 30 | 45 | 27 | 34 | 20.4 | 28.9 | 17.3 | 25.5 | 15.3 | 21.7 | 13.0 |
| 146lbs - 152lbs | 50 | 30 | 45 | 27 | 34 | 20.4 | 28.9 | 17.3 | 25.5 | 15.3 | 21.7 | 13.0 |
| 153lbs - 160lbs | 50 | 30 | 45 | 27 | 36 | 21.6 | 30.6 | 18.4 | 27.0 | 16.2 | 23.0 | 13.8 |
| 161lbs - 170lbs | 50 | 30 | 45 | 27 | 38 | 22.8 | 32.3 | 19.4 | 28.5 | 17.1 | 24.2 | 14.5 |
| 171lbs - 182lbs | 50 | 30 | 45 | 27 | 38 | 22.8 | 32.3 | 19.4 | 28.5 | 17.1 | 24.2 | 14.5 |
| 183lbs - 195lbs | 50 | 30 | 45 | 27 | 38 | 22.8 | 32.3 | 19.4 | 28.5 | 17.1 | 24.2 | 14.5 |
| 196lbs - 220lbs | 50 | 30 | 45 | 27 | 40 | 24 | 34.0 | 20.4 | 30.0 | 18.0 | 25.5 | 15.3 |
| Over 220lbs | 50 | 30 | 45 | 27 | 40 | 24 | 34.0 | 20.4 | 30.0 | 18.0 | 25.5 | 15.3 |

Fig. 18

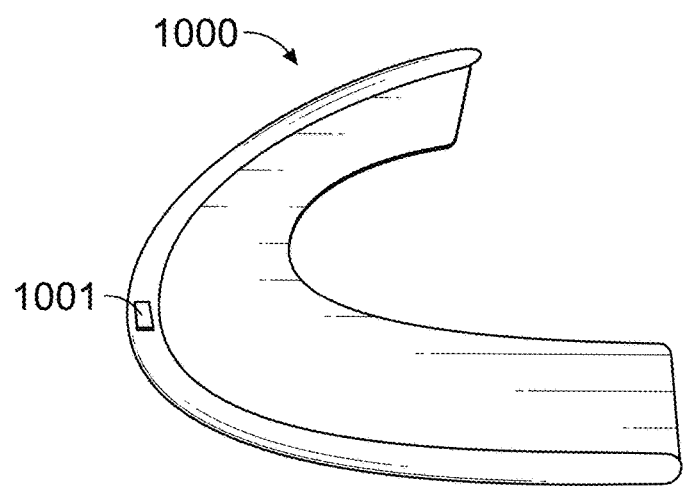
FIG. 24
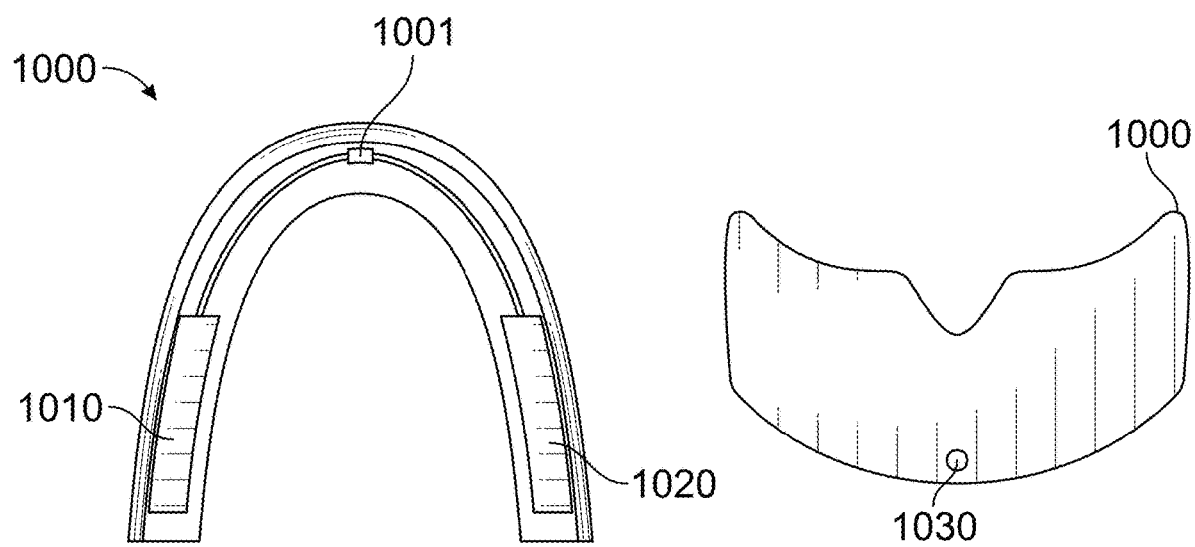
FIG. 25
FIG. 26

IMPACT SENSING WEARABLE DEVICE AND METHOD

CROSS REFERENCE TO RELATED APPLICATION

This application is a continuation of U.S. application Ser. No. 18/337,888, filed on Jun. 20, 2023, which is a continuation of U.S. application Ser. No. 17/443,019, filed on Jul. 19, 2021, which is a continuation of U.S. application Ser. No. 15/591,003, filed on May 9, 2017, now issued as U.S. Pat. No. 11,064,913, which is a continuation-in-part of U.S. application Ser. No. 14/063,354, filed on Oct. 25, 2013, abandoned, each of which is herein incorporated by reference in its entirety.

BACKGROUND OF THE INVENTION

Field of the Invention

This invention relates generally to wearable detection and alert electronics that double as protective gear for the prevention of injurious concussive forces. More particularly, this invention relates to a sports mouth guard with built-in on-board electronics for sensing lateral and rotational forces, transforming such data, and communicating estimated risk levels.

Description of Related Art

At all levels, athletics are seen as constructive methods of exercise. Sports encourage robust competition and health. Men and women, boys and girls participate in a variety of sports and athletic activities on levels ranging from the personal to informal pick-up game, to the more organized and professional levels. Given the variety of individuals involved, there is a diverse number and range of sports that we play. Some of these games involve high speed running. More physical sports may even involve purposeful or incidental contact between players and/or fixed objects. Such contact raises the potential for harm, including head and brain injury. While football is seen as the primary cause of concussions and long-term brain injury, it is less known that players in other sports also experience a high-risk for head injury and brain trauma. The incidence of concussions in girls' soccer is second only to football, and the combined incidence of concussions for boys' and girls' soccer nearly matches that of football.

Virtually any forceful impact to the head or body involves some risk level for brain trauma. Head injury may occur from collision with another player, an object, or even from a fall. Impact and rotational forces to the head are the leading causes for injury. Brain injury manifests as either neural, or most often, vascular injury within the head.

It is also widely known that the risk and severity of brain injury is related to the frequency and severity of repeated head trauma. A first blow to the head may modify the risk factors for future injury. For instance, a first incidental hit may lower the threshold for injury by a later fall to the ground. Repeated blows and impacts have a greater impact on the risk of head trauma. Even a minor blow, below the normal threshold for injury, may cause catastrophic brain injury if it follows an earlier risk-elevating first impact. Furthermore, biometric data (i.e. gender, age, height, weight, etc.) provide a separate method to determine impact threshold for predicting brain injury.

During play, head injury may manifest as a temporary impairment or loss of brain function; more severe concussions may cause a variety of physical, cognitive, and emotional symptoms. Unfortunately, some injuries cause no immediate or obvious observable symptoms, while even minor symptoms may be overlooked during the excitement of a game. The unknown consequences of prior impacts further exacerbates the risks, by failing to diagnose an injury and take corrective action.

Given the high-risk of injury in all sports and activities, from team sports to personal fitness programs, prior art solutions have not provided a solution that is flexible and precise enough for use in a myriad of routines. For instance, given the extent of electronics and monitoring systems required for head injury assessment tools, products to be worn by players often involve a skull cap or complete helmet. A helmet, while welcomed in permissive contact sports such as football, hockey and motocross, might be out-of-place for tennis, interfere with play for a sport such as soccer, and even presents an added danger on the rugby pitch.

Other products include multiple part pieces that are deployed on the player and can be cumbersome and/or complicated to employ. Additionally, other products do not provide a simple customizable single-piece portable solution.

Clinical tests have proven that the combined measurement of linear and angular acceleration has the most accurate prediction of concussion possibilities, compared to either of the measurements independent of one another.

Clinical studies suggest that sensors located in a mouth guard, as opposed to an accessory on a helmet or a chinstrap, have a higher correlation to the center of gravity of the brain. This is thought to be a result of the mouth guard's placement in relation to the rear molars, which are attached to the base of the skull.

It is therefore an object of the present invention to provide a single-piece mouth guard for identifying the risk factor for traumatic head injury.

It is a further object of the present invention to provide a diagnostic device that can indicate the potential for injury.

It is another object of the present invention to provide a personalizable risk detector that can reflect the risk factors based upon impact thresholds of a unique user.

It is yet another object of the present invention to provide an instrumented mouth guard that can be widely deployed to assess and indicate injury risk.

All these and other objects of the present invention will be understood through the detailed description of the invention below.

SUMMARY OF THE INVENTION

The present invention also includes various methods for detection, calculation and display of potential head trauma, preferably by use of a mouth guard with on-board sensors and diagnostic logic. The mouth guard is worn by the user and placed alongside the jaw or preferably molar teeth within the mouth. The user can preset a threshold scheme by putting or selecting a preferable predetermined biometric profile, preferably via on-board input button. The preset can be used to focus the diagnostic logic on particular thresholds of rotational and/or linear forces.

The may include on/off switch to conserve battery. Preferably off position option will allow any required memory to store attributes, such as biometrics, or previous shock instances. On/off switch may include an On button when pressed a first time to activate mouth guard until battery death, and a standby mode to allow low power mode between uses. Mouth guard in stand-by mode, preferably includes a low-G accelerometer function to allow automatic on-switching when sensing a major impact, or just even a minor motion indicating future use.

While powered on, the sensors continually monitor forces. Once the sensor experiences a force beyond the preset threshold, the logic function communicates with the mouth guard to cause the display function to illuminate in a predetermined scheme, such as a lighting scheme, preferable for an on-board LED lights.

The present invention includes a wearable form factor, such as gloves, knee brace, mouth guard, head band, etc. and a method of using implanted sensors in such a wearable form factor to collect and report data of impacts. The invention includes a method for quantitatively displaying impact experienced by a user wearing a mouth guard, in one preferred embodiment by contacting the mouth guard with a molar. First, preferably at least one predetermined impact first threshold is set. This predetermined impact first threshold may involve a calculation involving at least a linear force and a rotational force.

The form factor is then worn, such as a mouth guard being placed in the mouth. The wearable form factor preferably includes sensors and a display light. An impact is detected by the form factor and a determination is made as to whether or not such impact exceeds the threshold. If so, at least a light will be displayed on the form factor. Impacts may be sensed via a scheme of at least a linear force and at least a rotational force.

A predictive capability assessment risk function may be used to determine the risks. The predictive capability assessment risk function may include a consideration of the biometric data, which may emphasize or deemphasize linear vs. rotational forces, and/or the origin direction of an impact force.

The method may include sending a signal from the form factor to an off-board device for remote display.

The method may also include the setting of a second impact threshold, preferably involving a calculation involving at least a linear force and a rotational force. The second threshold may be lower than the first threshold. In a preferred embodiment, when the second impact threshold is met, the first threshold is modified (preferably to a lower threshold value. The wearable form factor may include various displays form the first and second, as well as the modified first impact threshold being met, preferably with a multi-color display (with a single color or display setting for each threshold type being met). Additionally, once the second threshold is met, the second threshold may also be modified.

In order to achieve the modification of the first threshold, information relative to a recent impact event is stored. Erasing stored memory will be required, such as after a set period of time, or upon manual or other coordinated override. User may selectively erase historical impact data and thereby may modify threshold alignment.

The method also considers biometric data, and may use such biometric data when setting threshold(s). Biometric data may include one or more of the following, weight, age, gender, height, skull circumference, and/or relative jaw pressure, or any other biometric data shown to help determine risk factors. Biometric data may be input via onboard buttons, and or remotely e.g. via remote Bluetooth connection.

DESCRIPTION OF THE DRAWINGS

A more complete understanding of the present invention may be derived by referring to the detailed description when considered in connection with the following illustrative figures.

FIG. 11 depicts a linear/rotational force impact scale indicating risk factors based on a combination of forces;

FIG. 12 depicts an alternative linear/rotational force impact scale indicating risk factors based on a combination of forces;

FIG. 13 depicts an alternative linear/rotational force impact scale indicating risk factors based on a combination of forces;

FIG. 14 depicts an alternative linear/rotational force impact scale indicating risk factors based on a combination of forces;

FIG. 18 illustrates a table showing varied impact thresholds and categorization of same, of an embodiment of the present invention.

FIG. 24 demonstrates a perspective view of another alternative mouth guard embodiment of the present invention.

FIG. 25 demonstrates a top view of another alternative mouth guard embodiment of the present invention.

FIG. 26 demonstrates a frontal view of another alternative mouth guard embodiment of the present invention.

DETAILED DESCRIPTION OF THE PREFERRED EMBODIMENTS

Figure 1:
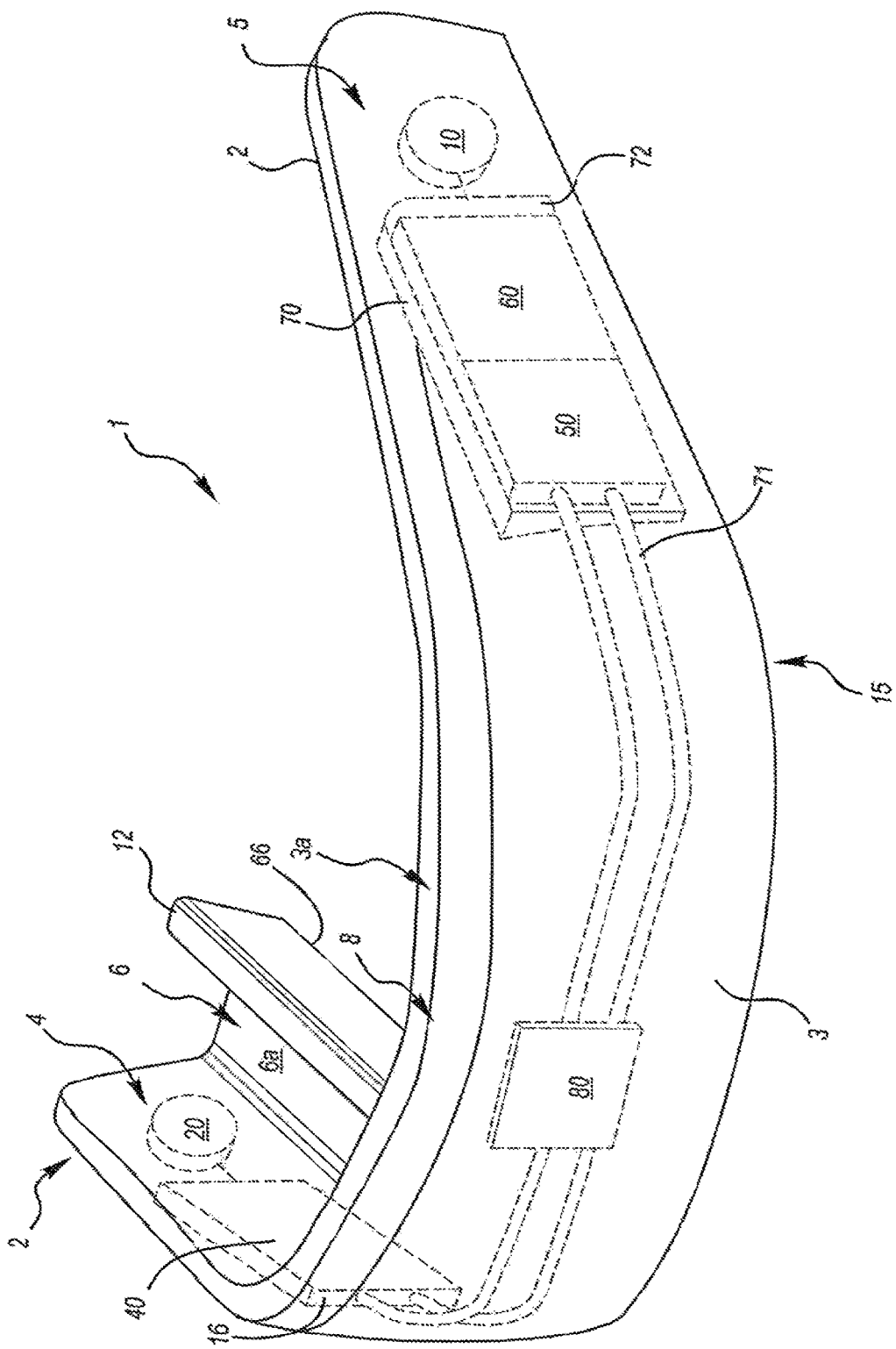
FIG. 1 depicts a perspective view of an embodiment of the present invention.

The present invention may be further described and understood by a limited set of preferred embodiments.

However, the embodiments described herein are intended for illustrative purposes only, and not to preclude other devices or embodiments that embody the invention herein.

The present invention aims to solve the problem of athletes returning to play when there is a high probability of head-injury. Our innovative device significantly increases the likelihood of early detection and the overall safety of athletes around the globe. Unlike a structural injury that involves a ligament tear or a shoulder sprain, brain injuries are not always apparent or easily detectable. Athletes continue playing, at times, without knowing they are at risk for further debilitating outcomes. Concussions are one of the most commonly reported injuries among the 135 million participants in team sports, including the 38 million boys & girls in youth athletics.

The present invention aims to solve the problem of athletes returning to play when they have a high probability of a head-injury. To accomplish this, we visually indicate when further evaluation is needed, using our High-Luminosity LEDs.

After an event, peak linear and angular acceleration, as well as already established bio-metric user data such as Age, Weight, Height, and Gender are uploaded to a remote or centralized database. Over time this database will help us improve the risk indication levels and thresholds.

The present invention includes user-specific adaptive programmable software, allows the user to establish a predetermined threshold based on their age, weight, and gender, or set their own desired levels of indication!

The present invention may include Bluetooth compatible hardware necessary to communicate with any BLE-enabled smartphone or device. Using Bluetooth low-energy, data & information can be pushed and pulled from the device.

A custom mobile application may be used to allow the user to download the event registry log of accelerations from the device. This will allow parents, coaches, and leagues to follow their normal concussion protocol, while having some quantitative data to consider.

A preferred embodiment uses a mouth guard to be placed into a user's mouth. The mouth guard is self-sufficient as a small portable useful item that can be used in a myriad of occasions and activities. It is anticipated that the user will be engaged in some sort of athletic activity. The mouth guard will be equipped with electronics that allow monitoring or sensing of forces, both linear and rotational. Preset thresholds, preferably personalized for the particular user, of combined rotational and linear forces will indicate various risk factors for brain injury. Furthermore, certain repeated hits of various or same intensity will indicate risk. Certain hit, or hits, may modify the risk threshold for future hits in the near term. When operating, the mouth guard may indicate status "ON" by lighting up an on-board display. Should a minor impact occur, the display may indicate so, for instance by blinking light, or light of another color. Should a major impact occur, the display would indicate, for instance in an alternative lighting scheme, i.e. color. The thresholds may be preset, and on-board memory may recall prior recent incidents to modify impact thresholds without further manual intervention.

A preferred embodiment of the present invention includes a mouth guard with on-board electronics and signaling, sensors and display lights. An LED indicates status of the system including powered status and risk factors. The use of on-board display alleviates the necessity for a third party device or extra component as is necessary in many competitive products on the market.

A first preferred embodiment of the present invention is presented in FIG. 1. Mouth guard 1 includes the usual components of many safety and impact reduction mouth guards known in the art. Body 15 is formed with a substance that preferably a soft rubber or plastic and acts as a resistor to electric current. Common materials include thermoplastics that melt and deform at a certain high-temperature to allow for an initialization in hot water bath of 180 degrees F. for about 30-60 seconds. Once in a more liquid and less viscous state, a user can customize the mouth guard by deforming the body to fit the actual contours of a user's teeth and mouth (not shown). In the preferred embodiment, the mouth guard will be customized for one user's fit.

Body 15 encapsulates flex board 70 and all components thereon. Flex board 70 may be limited to certain components, flex board may come in multiple pieces, each piece carrying one or more component, or all electronic may be including on a single flexible circuit board, preferably encapsulated within the mouth guard. Microcontroller 16 provides on-board preprogrammed logic to collect data from sensors, preferably including gyroscope 60 and accelerometer 50, transmitted along embedded wires 71. It is preferable that microcontroller also contains preprogrammed thresholds, and various sets of impact threshold data. The sensors, accelerometer and gyroscope, may alternatively be positioned intermediately within the body, or padding element, or at an interface between a hard section connected to such body. Alternatively, electronic components may be connected by wire, electronics pods, etc. instead of a flexible circuit board.

Mouth guard may be formed in three basic steps. First, the flex-board and all components are arranged. Once arranged, the electronics may be set within a bottom mold. The bottom mold is then filled to complete the lower portion of the mouth guard with a material to form the body. Finally, an upper chamber mold may be used (preferably once the lower portion is flipped) to complete the body portion. Once completed, the body is then cleaned, and the action/power buttons identified and ensured for indentation. Alternatively, the body may be formed in a single injection mold around the electronics, or any other method as known in the art. The electronics may be protected by a casing or shield to avoid overheating during production encapsulation. The casing may adhere to, or otherwise be absorbed into the body to form a tight fit between the electronics and body. The electronics, particularly sensors, must adhere strictly to the body to allow for precise measurements of force on the body. Therefore, outside surface of the sensors may be exceptionally thick to expose to the body during formation/injection, or the surface may be scored, pocked, or otherwise detailed to allow for snug tight fit with body.

Figure 2:
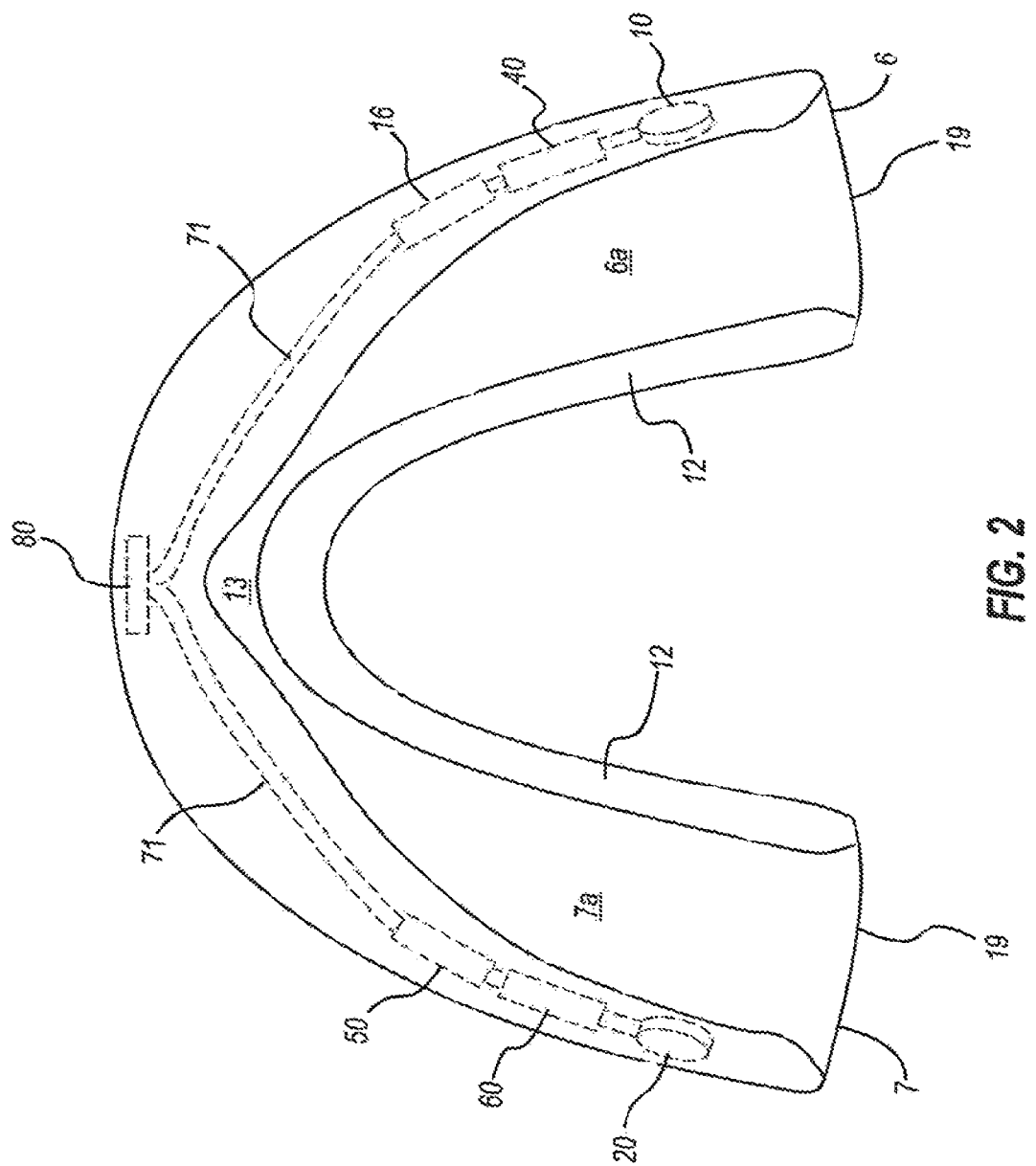
FIG. 2 depicts a top view of an embodiment of the present invention.
Figure 5:
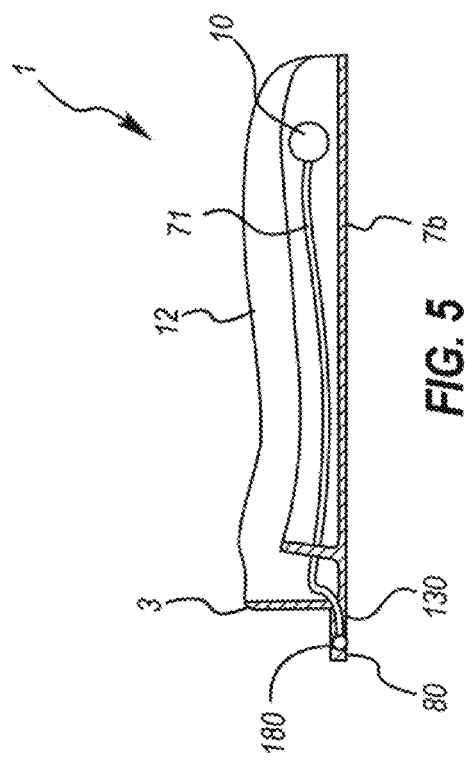
FIG. 5 depicts a side view of an embodiment of the present invention.

Referring to FIGS. 1-2, mouth guard 1 includes a right bite pad 6 and a left bite pad 7 to contact user's teeth, preferably molars and/or bicuspids. Bite pads 6 and 7 may be partially deformed in the initialization procedure to better conform to the contours of a user's mouth. Bite pads and side shields will be thick enough to allow such deformation without exposing electronics. A channel may be formed to receive the teeth. It is also contemplated that bite pads may include at least two substances, a first at bite pad top 6A and 7A, and a second material such as a hard plastic or shield at bite pad bottom 6B and 7B (seen in FIGS. 1 and 5). Front bite pad 13 is similarly formed to accommodate incisors and cuspids.

Side shields 4 and 5 may provide housing for on-board electronics and may also be made of deformable plastic or rubber, or other material or composite. Alternatively, side shields will be made of a more permanent solid material for the protection of the electronics, and may or may not be coated with the deformable material for better user sensory feel along users inside cheeks. Interior top ridge 12 of front shield 3 includes protection and front shield 3 provides for encapsulation of display 80. Display 80 may be set right along edge 3A or more centered within front shield 3. Front shield 3 preferably includes indent 8 at the top to accommodate the superior labial frenulum. Interior top ridge 12 should be soft enough to accommodate contact with user's soft gum or gingiva. In this embodiment, the bulk of the electronics are positioned on the sides and front of the mouth guard to avoid the risk of a hard bite to damage components. Alternatively, the electronics can be placed in the front, or below with a more solid bite pad, or in combination of the two, or elsewhere.

Microcontroller 16 preferably collects information from sensors, performs necessary calculation, and when impact data received from sensors indicates a hit beyond a threshold, microcontroller 16 sends signal along wire 71 to display 80 to cause display 80 to demonstrate a predetermined indication scheme. Most preferably, the data is passed along in real time, although in some versions the data is stored in a memory and accessed at a later time. Memory is preferably stored in or accessed by the microcontroller, but may also be included in a separate element (not shown) such as RAM chip(s), flash memory, etc.

Preferably display 80 includes light-emitting diode display. Action button 10 may serve as an on/off toggle switch for the mouth guard electronics. When in the off-position, the mouth guard should still serve the standard purpose of a simple mouth guard, but not collect or handle impact data. Input button 20 allows user to communicate and send direct data in predetermined signal language to the microcontroller to accomplish certain tasks such as setting a predetermined biometric set of thresholds, reset the device, reset the timer, or in some embodiments, set the device to standby mode.

Various demographic modes are contemplated for customizable programming of risk factors/thresholds. For instance, there may be a high, low, and average threshold category for weight. There may also, or instead, be a gender category, and/or an age category, etc. In one embodiment, to program the mouth guard, press the action button for 10 seconds. The indicator will blink white to indicate that programming is now available. Press the action button once for low mode, twice for medium/average mode, and three times for high threshold mode (weight). Each time the button press is activated, the display may change colors, i.e. turn red briefly to indicate acceptance of a button press. Holding the button an additional at least 10 seconds, will set into a second mode to indicate gender, i.e. once for male, twice for female. When inputting a second demographic data set, it is contemplated that a second color will blink in display, i.e. blue blinking. When inputting the third demographic set, i.e. age, the same rules will apply for age categories, i.e. under 12, 13-16, 17-22, 23-35, and 35+. The mouth guard is sold with an instruction manual to allow for activation and customization, as well as instructions to reset the customizable category. Depending on the customized demographic data of a user, the impact thresholds will be set. In the embodiment with RAM memory requiring power to retain information, it is contemplated that a low power source will maintain demographic data in standby mode. Impact thresholds will be set to raise or lower thresholds for minor and major hits, and/or modify the risk curves based on gender or age data, for instance see curve modification indicated in FIG. 12.

Further, preferably on flex board, is power source 40, preferably a battery. Power source 40 preferably provides power as direct current to microcontroller 16, display 80, and preferably sensors 60 and 70. Battery voltage may be below 10V and preferably between 1V and 6V. A voltage regulator (not shown) may be included to allow a single power source to provide power for all components.

Power source 40 may be a simple coin cell battery. Alternatively, power source uses inductive or wireless charging. Inductive charging allows a rechargeable guard while still not having any exposed ports. In a preferred embodiment, there may be a complementary charging station, i.e. pad or mouth guard container case, with built in inductive capability.

In an alternative embodiment, antenna 71 may be included along flex board 70 to allow for remote transmission from or to on-board electronics. For instance, remote data or instructions may be programmed to the mouth guard from a remote component, such as over wireless frequency Wi-Fi, or other electro-magnetic transmission, to communicate data to the on-board micro-controller. Another use may be as a source of information to communicate impact data and risk factors to an off-board monitor.

Microcontroller 16 preferably includes built-in memory capacity. Preferably, a portion of the data in memory will be hard coded. Preferably the predetermined biometric scales and impact threshold, as well as the logic equations for one or all of the biometric sets will be hard-coded into memory. The memory may be able to hold, and selectively erase, historical impact data. It is envisioned that through, input button, the memory may be reset to erase short term memory of historical impacts. It is also contemplated that the memory may have on-board clock timer that will be used by microcontroller to selectively erase historical impact data more than a predetermined time length, i.e. more than 24 hours, while using more recent data to help determine if an impact threshold has been met.

Figure 3:
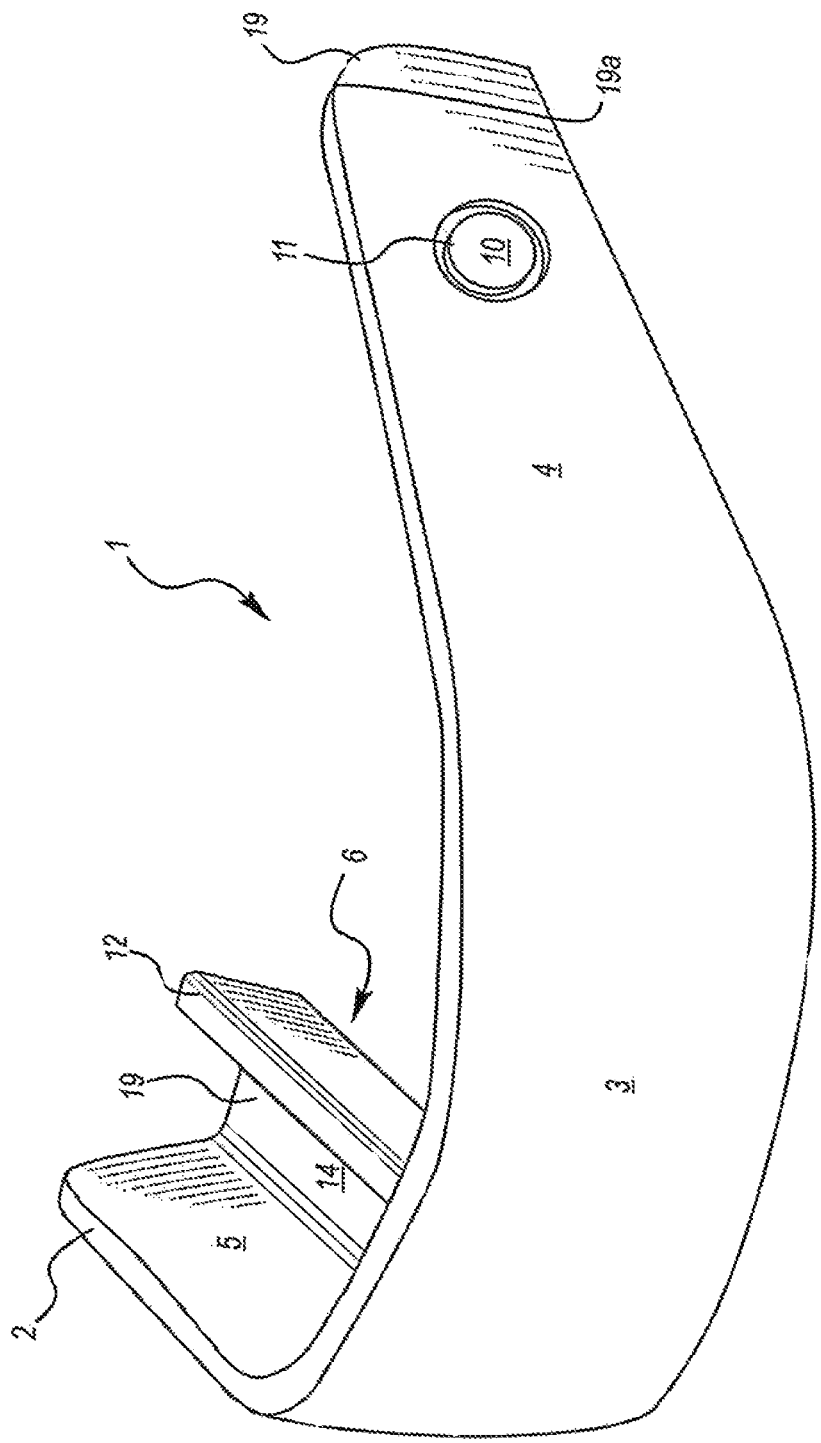
FIG. 3 depicts a perspective view of an embodiment of the present invention.

Embodiment shown in FIG. 3 shows the user impression of mouth guard 1. Action button is shown on the outer side of the mouth guard and recessed within button indention 11 on the circumference of the button to preserve the feel of an ordinary mouth guard without any unnecessary user discomfort. Excess molar portion 19 may be included to allow users with a smaller mouth cavity, or preferring a smaller mouth guard to disregard, remove and eliminate excess portion. Components may be arranged to allow for a variety of user sizes, with sensors still in contact or coupled to proper bicuspid or molar teeth to allow for accurate measurement of forces. Indication bar 19A may show user the limit or portion to remove without affecting on-board component otherwise hidden within guard.

Figure 17:
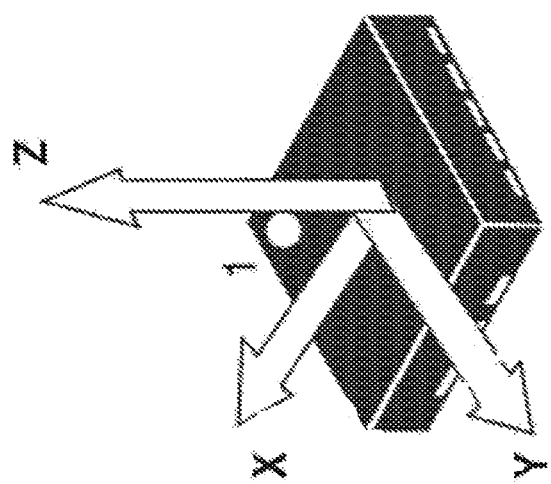
FIG. 17 depicts a preferred accelerometer with the direction of detectable accelerations.

As seen in FIG. 17, an accelerometer serves as a linear forces sensor. Preferably includes sensors for three dimensions. Preferably, the sensor fits within the mouth guard connected by wires to the microcontroller and other components. A small thin accelerometer such as the a 3×3×1 mm3 motion sensor with a digital output, low power requirement, high-g, and 3-axis accelerometer, as known in the art, is preferred to suffice. It is preferred that supply to the accelerometer is below 2V, around 1.5-1.8V, but may be as high as 3.6-6V. It is contemplated that in a low-power mode, the accelerometer can suffice on as little as 10 micro amps The accelerometer may be able sense forces as low as 10G, and to handle forces as high as 100-400G, and have a high shock tolerance above 10000. A sleep or stand-by mode may be used to conserve power. The accelerometer may have on-board logic and memory to log impacts, or to selectively report only impacts above a certain threshold, to save power. It is contemplated that the accelerometer will transmit digital signals.

Thresholds for linear forces for an average adult male may be set as high as 100 to 300 G forces. Preferably the sensor is able to handle and distinguish forces at this great shock within a 10-20 G range. Lower shocks with impact G force of less than 100 will preferably be selected within 5G. While the thresholds are listed in this specification and on the Figures, they are in no way intended to limit the threshold settings ranges for practice of the present invention. As studies, data, and even personal preferences evolve, various threshold levels of acceleration and rotation may be programmed into an embodiment of the present invention.

Figure 16:
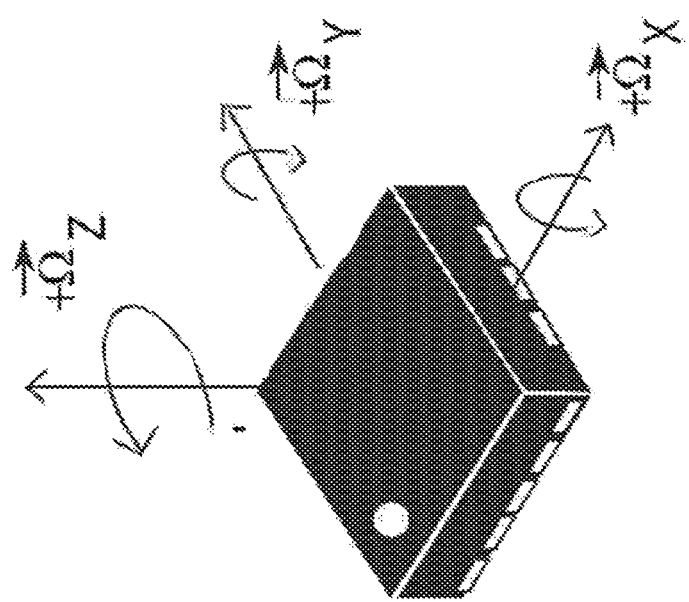
FIG. 16 depicts a preferred gyroscope with directions of detectable angular rate.
Figure 19:
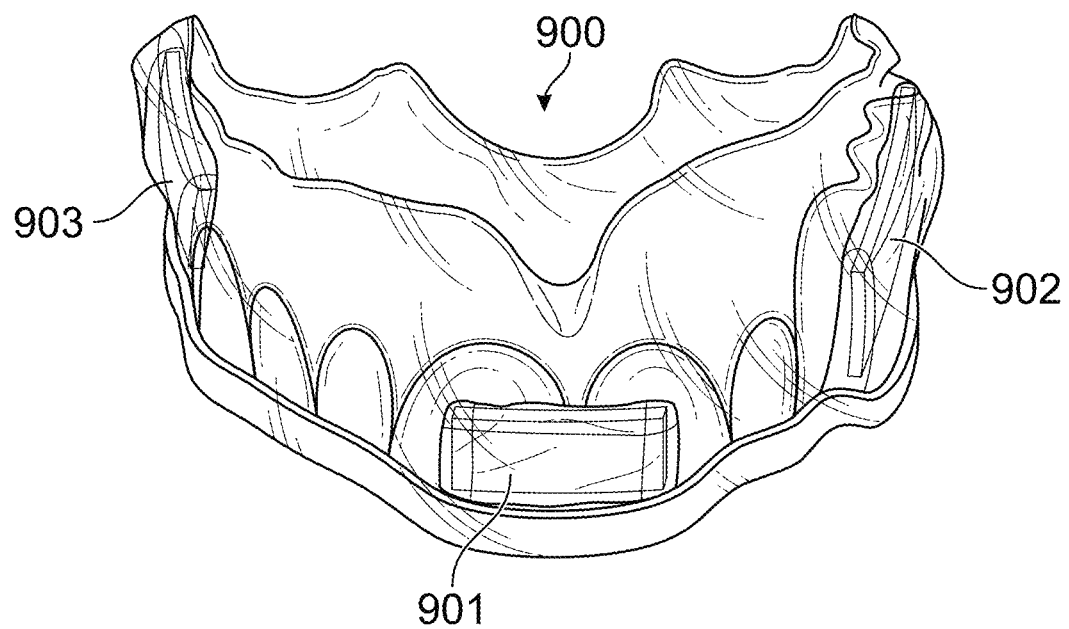
FIG. 19 shows a frontal view of an alternative mouth guard embodiment of the present invention.
Figure 20:
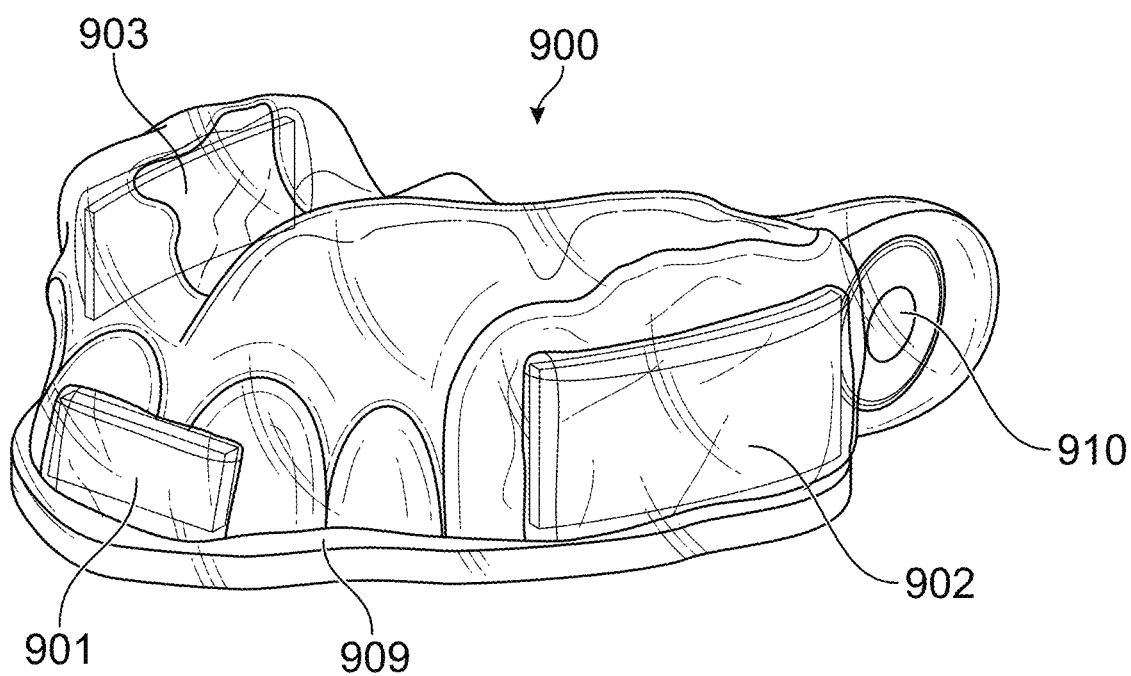
FIG. 20 shows a perspective view of an alternative mouth guard embodiment of the present invention.
Figure 21:
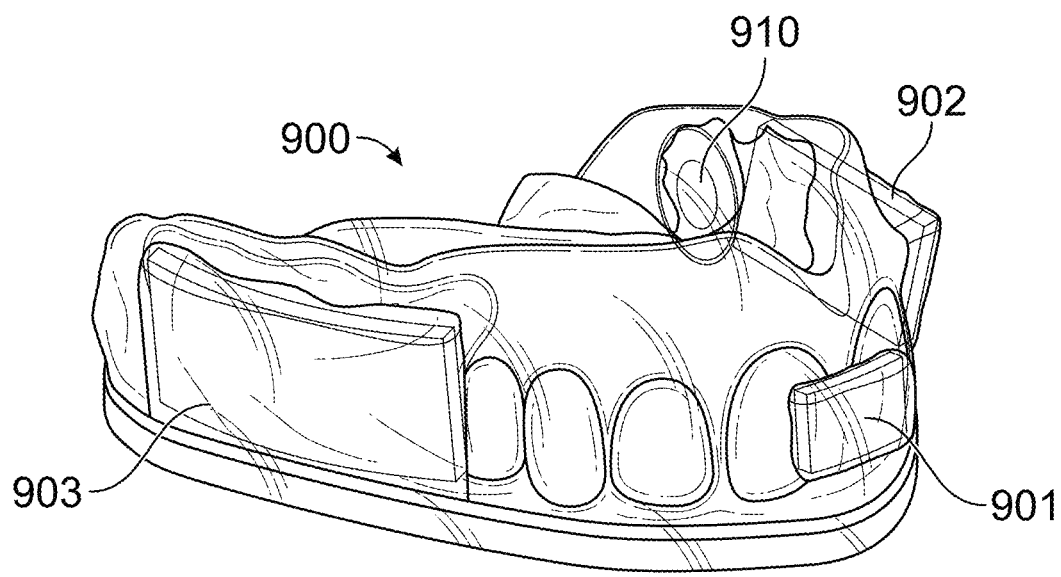
FIG. 21 shows another perspective view of an alternative mouth guard embodiment of the present invention.
Figure 22:
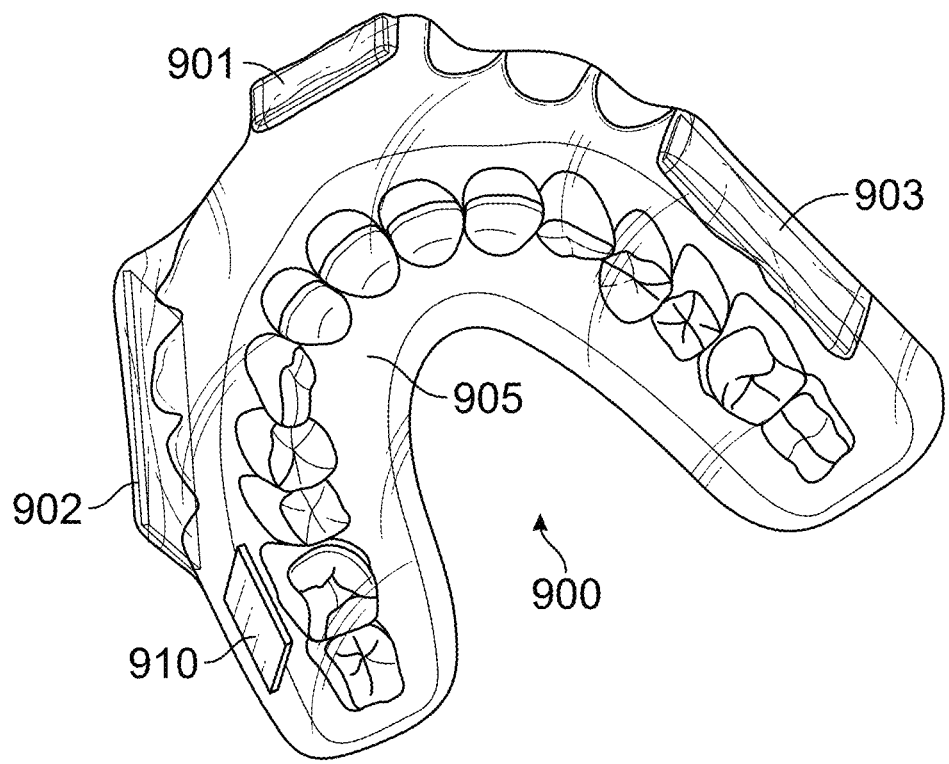
FIG. 22 shows a top view of an alternative mouth guard embodiment of the present invention.
Figure 23:
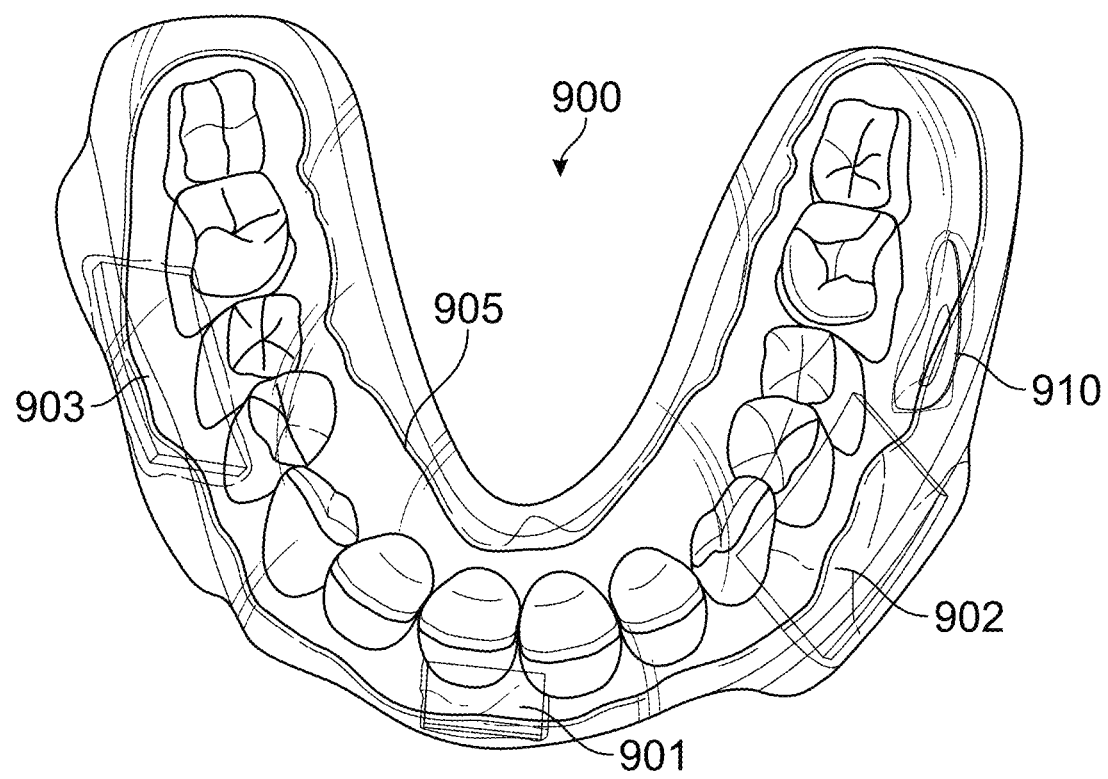
FIG. 23 shows another top view of an alternative mouth guard embodiment of the present invention.

As seen in FIG. 16, the gyroscope should have similar electronic, power, output, and sensor characteristics as the accelerometer. The gyroscope will sense three-axis rotational acceleration, typically considered in radians (rads) per second squared (sec2). Similar in size and shape to the preferably with the linear sensor/accelerometer, the gyroscope will also preferably fit on the flex board The gyroscope either outputs information on the three-dimensional level, or includes in component logic to output a single data packet to include a total G rotational force profile. Given the fixed orientation of the gyroscope in the mouth guard and known placement in the mouth, three-dimensional forces may help determine the location (source) and direction sensed by an accelerometer can on its own or in combination with gyroscope help calculate force source and risk potential. Typically, in forceful impacts, rotation can reach accelerations on the order of thousands of rad/sec2, and the gyroscope will preferably be able to determine rotation to the 10 rad/sec2 precision. In some embodiments, the gyroscope will include on-board memory as the accelerometer, and may also include temperature sensor that may be used to help calibrate impact data. It is contemplated that the gyroscope and accelerometer will perform under the same specifications and actions.

As seen in FIG. 1, it is contemplated that the position and orientation of the gyroscope be fixed within mouth guard 1, possibly held in place by flex board 70, wires 71, and/or relation to other components. This positioning may help determine the source or direction of impact. Data from the gyroscope, accelerometer, or a combination of data between the two (possibly calculated within the microcontroller) can help determine the direction of impact to the head or body.

Figure 7:
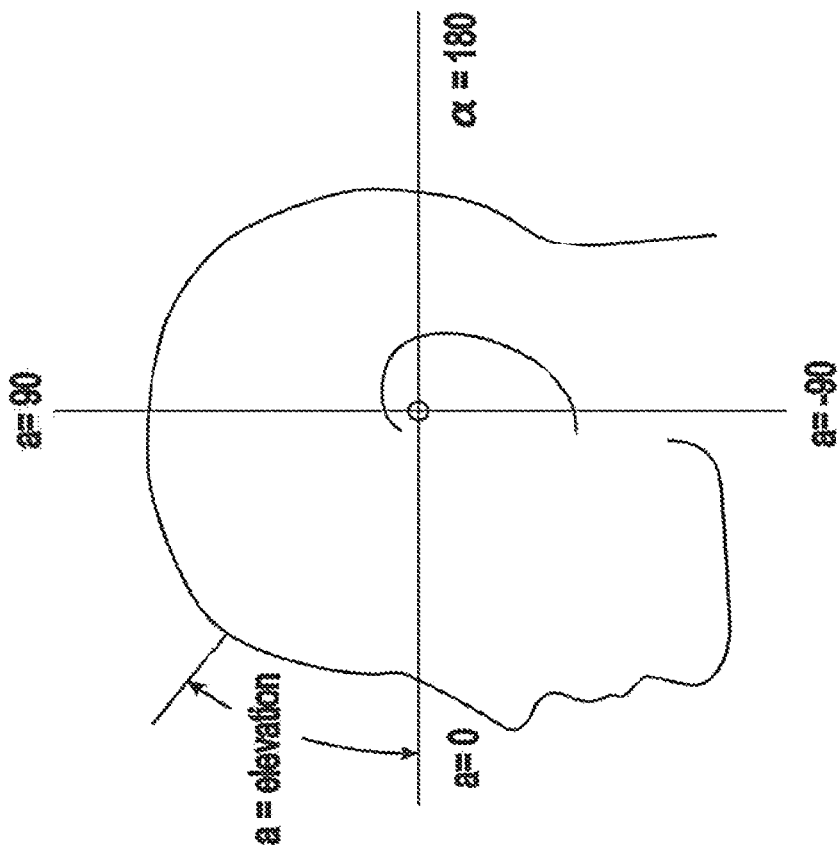
FIG. 7 depicts a side view of a human user head.
Figure 8:
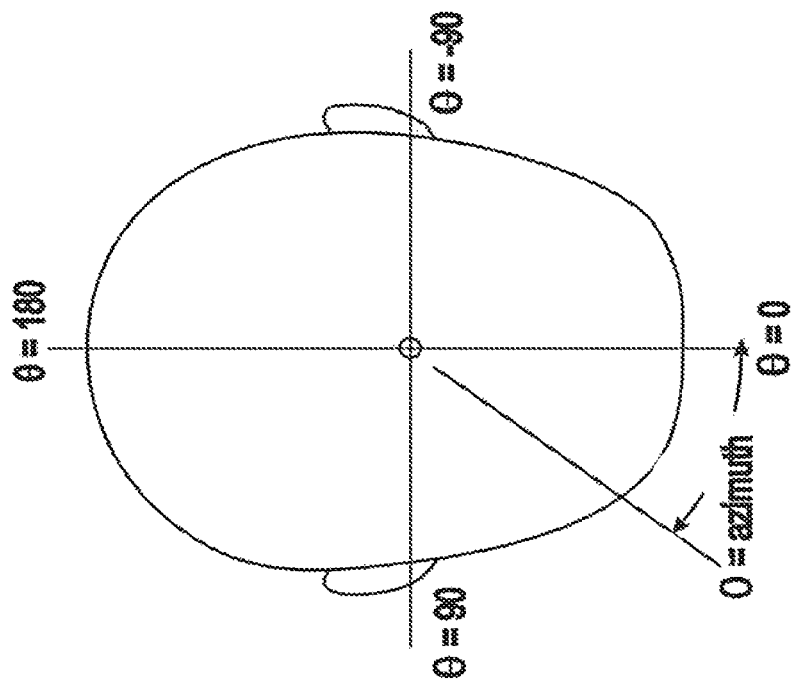
FIG. 8 depicts a top view of a human user head.

As seen in FIGS. 7 and 8, direction of impact may have an impact on the threshold for risk. For instance, hits in front (experienced as directly back and down) may prove having a lower risk of injury at a high impact force, as forces to the side (experienced as a sharp turn and/or sidal force) may raise the risk (and thus lower the threshold) for risk. FIGS. 7 and 8 indicate a map of the human user head which can help provide illustration for categories of direction hit. Impacts with an elevation greater than 65 degrees may be categorized as a hit to the top, whereas those below 65 degrees, and having an azimuth between-45 and 45 degrees would be categorized as impacts to the front. Elevation below 65 degrees and azimuth between −135 and 135 degrees might be categorized as hits to the rear. The remaining impacts might be categorized as shocks to the side of the head, given the symmetry of the human head about the sagittal plane.

Figure 4A:
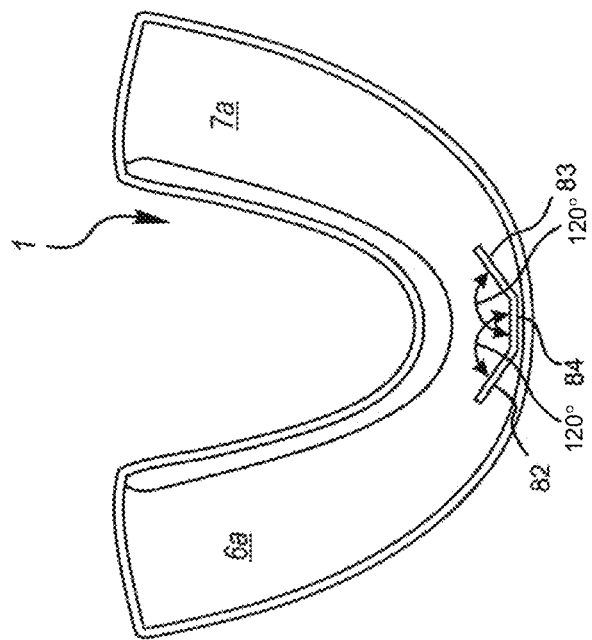
FIG. 4A depicts a top view of an embodiment of the present invention.
Figure 4:
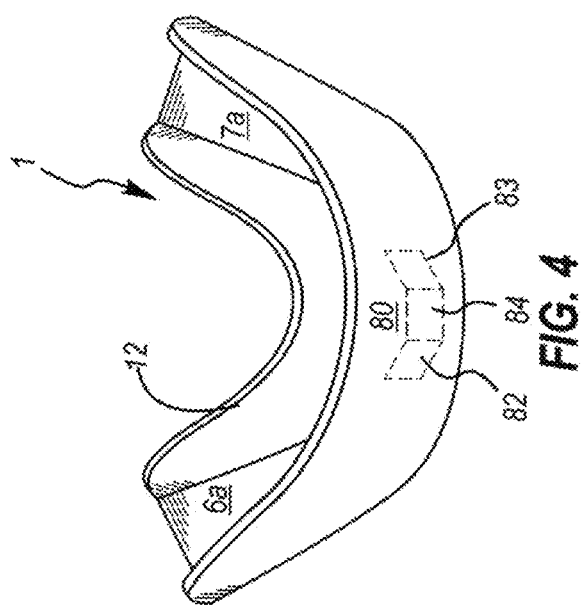
FIG. 4 depicts a top perspective view of an embodiment of the present invention.

Preferably a single 3-color LED capable of RGB colors, including ability to combine to provide virtually all colors and white. As seen in FIGS. 4 and 4A, three separate LEDs may be provided. Orientation of LED with 120 degree, may be utilized to provide 180 degree or further display viewing, up to and perhaps more than 300 degree viewing, plus the scattering effect on the skin. LEDs may be powerful enough to be viewed when covered by the lips/cheek as the user's mouth is closed.

An alternative display configuration is shown in FIGS. 4-4A. In this instance a triple angled display screen, preferably including a single LED display on each face, is arranged to provide notification to others at the front and sides of the user. An embodiment of the invention also contemplates that the display indicator may be bright enough, or use vibrations with a separate component, to indicate to a single user when in use in an individualized capacity. The display 80 includes front display panel 84, as well as right and left display panels 82-83. In a preferred embodiment, the arrangement is set where by panels are each offset at an angle of about 120 degrees to provide an array of viewing angles. The display may be encapsulated in the padding material, or may be attached on the outside of the display.

Figure 10:
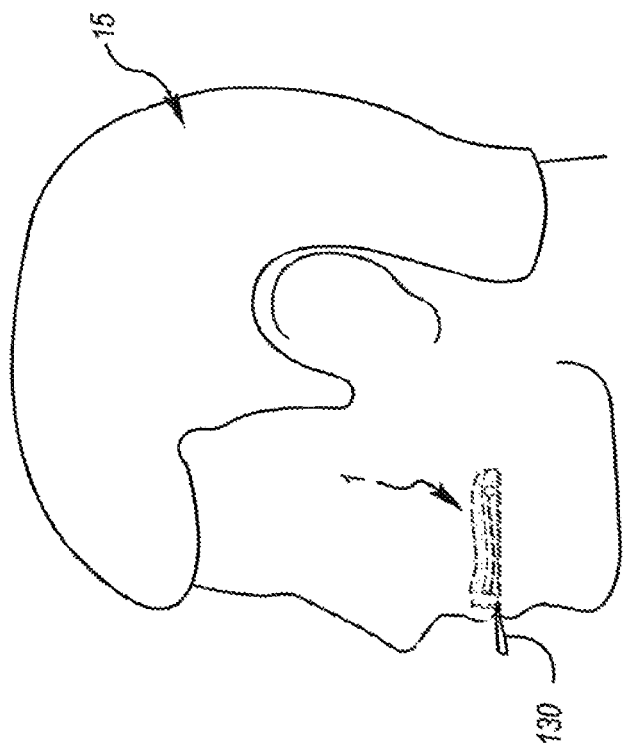
FIG. 10 depicts a side view of a human user bead engaging an embodiment of the present invention.
Figure 9:
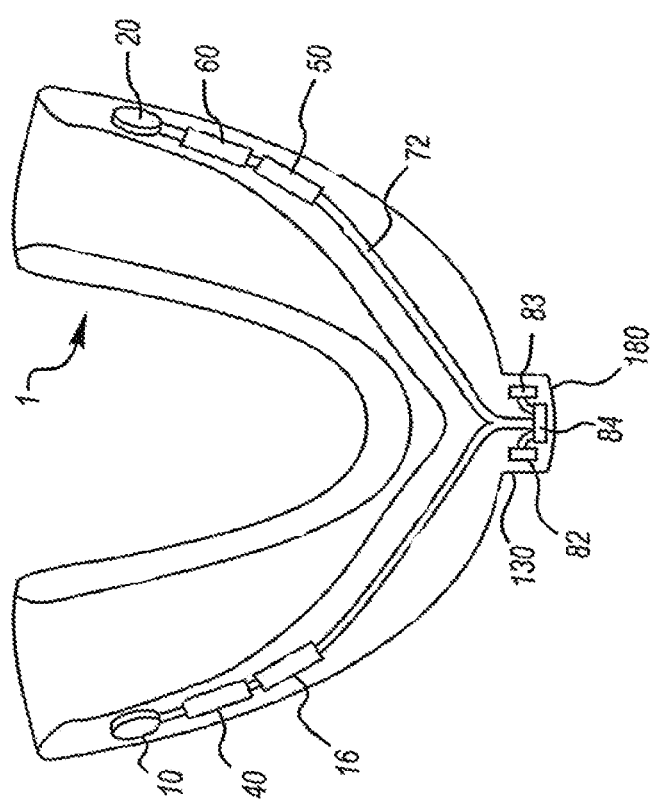
FIG. 9 depicts a top view of an embodiment of the present invention.

An alternative embodiment is shown in FIGS. 9-10. Mouth guard 1 includes extended tab 130. Extended display 180 is connected to microcontroller, or other component to activate display when necessary. In the embodiment shown in FIG. 9, extended tab 130 includes extended display 180 with three separate LED display panels 84 facing directly forward, and 82 and 83 as right and left displays preferably arranged perpendicular to the front display.

Figure 15:
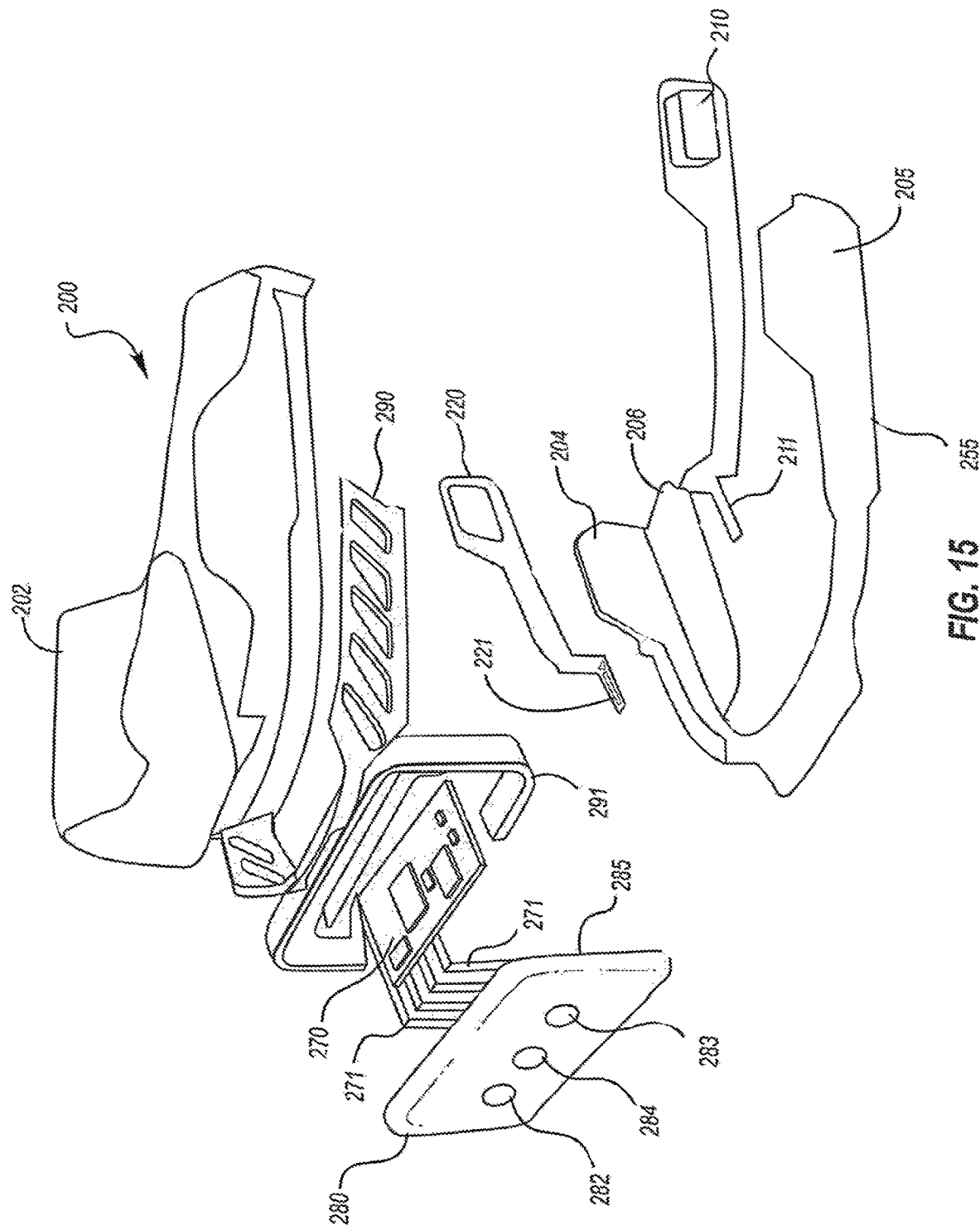
FIG. 15 depicts an exploded view of an alternate embodiment of the present invention.

In a preferred embodiment as shown in FIG. 15, three LEDs. A single small board contains all of the components towards the front of the unit all in one location. The present invention may also utilize a screen of multiple LEDs, or alternative light source, to display graphics, colors, or words and/or lettering to communicate risk status. Mouth guard 200 includes a encapsulation material body 202 that holds components. Protection shield 290 serve to provide substance and strength to the body to protect components. Action tabs 220 and 210 serve to allow user input into device. Side shields 204 and 205 may contain conductive material to act as a single antenna 255, or may serve as protection for signals transmitted to flex board 270 from pads 210 and 220 via contacts 211 and 221. Contacts 211 and 221 mate with board 270 which houses the microcontroller and all sensors and power sources, electronic components, etc. Wires 271 communicate with display 280 (off of board) to allow three LEDs 282, 283 and 284 to display status. Frame 291 serves to further protect and hold board 270 in place. In a simple version, each LED may transmit a separate color, in more advanced embodiments, the LEDs each contains multi-color functionality (three lights to create all colors including white), or display panel 285 may contain a myriad of arrayed LEDs or other display lights or indicators to demonstrate various symbols, numbers/words, etc. The display board may also indicate team affiliation (colors) or be used for novelty, i.e. fangs, blood, grass, fake teeth, tongue, cigarette, etc. or be used to display a message or other personalized feature.

Figure 6:
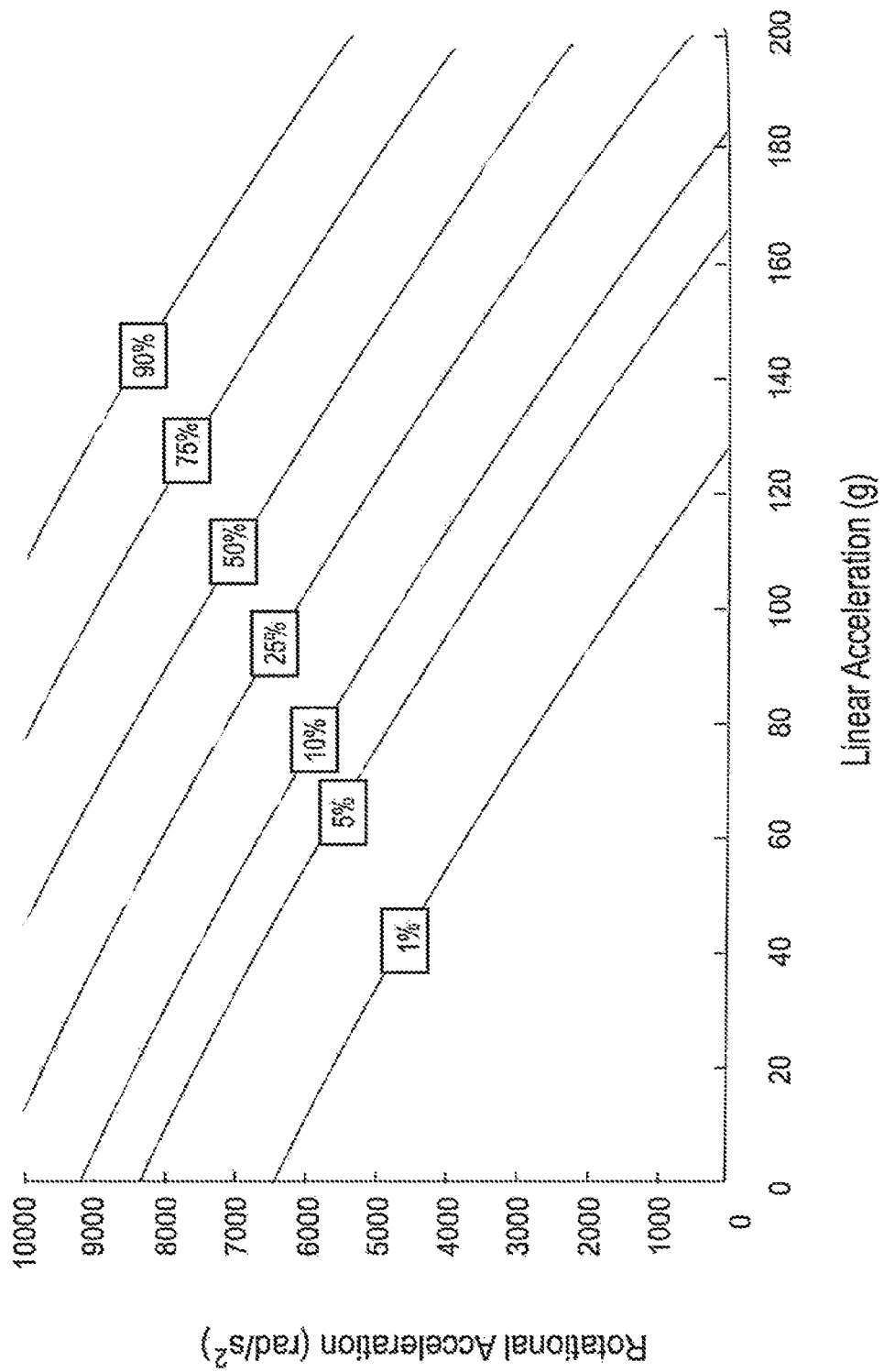
FIG. 6 depicts a linear/rotational force impact scale indicating risk factors based on a combination of forces.

As seen in FIG. 6, risk factors for individuals experiencing shock trauma to the head or body typically manifests as a combination of linear and rotational forces. Even straight shots typically include a partial rotational element given the anatomy of the head and neck. However, straight shots, as well as shocks that have little to no linear component and are merely a rotation will also be included as examples in the logic. Peak rotational velocity may also be measured and combined into the risk algorithms The predictive capability assessment risk function, absent corrections as detailed above and those known in the art, can be displayed as an equation. Where b0 [beta 0], b1, b2, and b3 may be regression coefficients determined using a generalized linear model technique, a is peak linear acceleration, a [alpha] is peak rotational acceleration, and CP is the combined probability of concussion. Less, or additional, factors may be used depending on the number of biometric data points included in the calculation.

$$CP = \frac{1}{1 + e^{-(\beta_0 + \beta_1 a + \beta_2 \alpha + \beta_3 a\alpha)}}$$

While linear acceleration is not a significantly worse predictor of concussion than the combined probability of linear and rotational acceleration for concussion for all data sets, and rotational acceleration alone is associated with the smallest predictability, the purpose is for a predictive capability with a low false-positive issue. Such accurate information with low false-positive indications should lead to greater adoption and continuing use of the product. Using rotational acceleration as a brain injury predictor results in the greatest false positive rate associated with high true positive rates, while using the combined probability of concussion produces lowest false positive rates in all head impact telemetry data sets. Findings clearly indicate the a combination of both linear and rotational forces add value to the safety of the device, particularly among young athletes, who will resist sitting out of a game due to a false positive. The goal is to prevent players staying on the field with a concussion, while simultaneously encouraging product adoption and use.

For illustration, using a "red" display might indicate that the risk threshold is met. Using rotational acceleration measurement leads to more often "going red" and the player not having a concussion, while simultaneously having a more hits that previous would not have "gone red" head only linear acceleration been used, resulting in a concussion. Additionally, the curve may be modified to include threshold of a single source, i.e. accelerometer or gyroscope, as shown in the intersection of the probability lines of FIG. 6 with the axis.

Plotted out, risk function predicts probability of concussive impact. As shown in FIG. 6, for a typical user, the thresholds for various risks are displayed charted as a combination of linear and rotational accelerations (indicating force). In another preferred embodiment, the user may preselect the level of probability for the various risk levels. In a preferred embodiment, a set risk factor, i.e. 50% may be set as a major hit, as recorded by the sensors and calculated by logic at the microcontroller. A signal would be sent to activate the display indicator to show a significant hit, such as "RED" light. A hit in a range below a certain low threshold, i.e. below 25%, but above 10%, might indicate a preparatory hit that reduces the threshold and increases the risk factor for a second force causing a concussion. In this instance, the major hit threshold might be reduced, i.e. from the 50% equation level to a 40%, etc. A minor hit, i.e. between 25%-50% probability of concussive brain injury, might signal a first warning display, i.e. blinking light, and also may modify the thresholds for major and minor hits in the same fashion of a low hit, or otherwise.

Typical procedure of risk factors, impact thresholds, are demonstrated in FIGS. 11-14. FIG. 11 demonstrates a typical mainline threshold. Upon modification based on biometric data, the threshold may shift simply, as shown in FIG. 13 or dynamically, as in FIG. 12. It is contemplated that certain demographics may be more or less susceptible to injury based on linear vs. rotational forces, i.e. children may be more susceptible to rotational forces, so the modified risk factor/threshold might be lowered disproportionately in the rotational dimension as compared with the linear dimension. A first impact of significant shock may impose a shift of the major risk threshold simply as in FIG. 13, or may also dramatically alter the probability function as shown in FIG. 14 demonstrating that a portion of the brain susceptible to specific type or direction of impact may be at a higher risk.

The mouth guard will preferably be powered by on-board power source, such as a battery. It is compatible with an embodiment with out on/off switch could have on switch such as broken capsule that may be a one-time use as switch. The capsule may contain a resistor that, when broken, serves to transmit electrical power and thereby power on the device. If using RAM for memory, a low-power standby mode may be used to conserve power. Action button, i.e. 10 or 20 shown in FIG. 2 may be used to power down the device, or device may use a clock timer to monitor activity and auto power down after a set period of inactivity, i.e. four hours.

Various LED Display settings are contemplated. For instance, when the device is on and actively sensing forces, the display may show a solid blue light. This will indicate that the device is on and functioning. Before activity ensues, each player may check the status of the device, and players with a non-functioning mouth guard may be identified. A minor hit may cause a different display, i.e. blinking red/green or alternative colors. The differing display may be reset, should the player chose to resume play by either waiting a set amount of time, i.e. 5 minutes, or by resetting via the on-board action button. During play, if there is a first concussive shock that triggers the alternate (lower) thresholds, this may be reset by action button, i.e. holding it down. This may be done when the thresholds are not properly set, to avoid false positives, or to allow multiple users to use the device. When a major hit occurs, a solid red display light might indicate high risk of injury and alert player to be removed from play. Further advances with multiple LED may allow for a more detailed display, i.e. not only using color, but also a letter, symbol, or word, or percentage risk factor, etc. may be displayed. This advanced multi-LED display can also be used effectively when initially setting risk thresholds manually for better interactivity.

It is preferable that the power source include an on-board battery, preferably Nickel-Cadmium as known in the art, to provide necessary voltage power for all components. It is contemplated that in a preferred embodiment, the battery will be built into and integrated encapsulated within the mouth guard. In an alternative embodiment, the on-board battery will be rechargeable. The recharge may be accomplished by a hidden plug in accessory access port, preferably behind a flap section of the mouth guard material (not shown). In another alternative embodiment, the battery can be recharged remotely by induction, preferably through a complementary pad docking station, or alternatively within a mouth guard case.

In an alternative preferred embodiment, there will be a complimentary display function on a remote display piece. In this instance, the on-board, or integrated built-in, antenna transmits a preferably electro-magnetic signal to the remote receiver which is in turn connected to the display. An example might be a remote WiFi receiver, or a BLUETOOTH receiver such as a common handheld device, e.g.

cellular phone, or handheld tablet, etc. Note: the type of devices, components, including sensors, displays, power sources, related devices, etc. are herein shown for illustrative purposes, and should not be read to limit the present invention to any specific device or component.

The alert and indication are part of the present invention. An LED display is contemplated as a preferred embodiment of the alert method, but future and more advance device could integrate alternative indication, such as: text, email, push-notification, sending data to an external app, and that app then alters the individual risk factors. The present invention has been described in the above illustrative embodiments, but should not be considered to be limited in any way therein.

The device will constantly sample rates of acceleration. As acceleration increases, the sampling rate will increase proportionally. If the peak of that acceleration breaches a threshold, the LEDs will change colors. These thresholds are established by using the FIT pre-determined threshold or can be user specified. In addition to peak linear and angular acceleration, the duration of the event will also be transferred to the mobile application.

After an event, data may be uploaded to a centralized database. This information will be used to improve the accuracy of user thresholds. Quantifiable data will be readily at hand. This allows users and interested personnel to make an informed decision while following normal concussion protocols.

We know that there is documented evidence showing that teenagers are susceptible to concussions at a lower level of force than adults are. Furthermore, the belief is that children are more susceptible than teenagers, based on the same logic. This is not yet proven, because there are no tests, or current data set, for youth head impacts. The concept is that lower impact thresholds are required to cause (serious) injury in children as opposed to adults. Children can be defined as low as 0 years of age, but are more appropriately between 4 and 12 years of age. Teens might be defined as 13 to 18, give or take a few years. Teen may also include ages up to 25 years. Furthermore, elderly, over 55 years of age, or similar advanced age, may indicate further susceptibility.

Furthermore, there is documented evidence showing that females are more susceptible to concussions than males (i.e. less force is required to concuss a female than a male). This may be due to the skull thickness as a result of testosterone.

The CDC estimates that 50G forces is a fairly broad "baseline" for adult male concussive force. Concussions may not occur at 50G forces, and concussions may occur below 50G forces, however they have drawn a line in the sand that 50G forces is a significant level of force. For that reason, we selected 50G forces as the starting point for our adult male red indication. Given that science cannot accurately determine at what point a concussion has occurred (various degrees of concussive damage and symptoms may be blurred), our thresholds are not meant to "diagnose" any sort of condition. Rather, the lights (and corresponding values) are meant to provide a visual display of the force an athlete received.

Based on the knowledge that sensitivity to impact force increases as age and weight decrease, sensitivities are built into the indications.

As shown in FIG. 18, the levels at which indications occur is shown by example (numbers are for illustrative purposes, and should not be read to limit invention thresholds unless explicitly claimed). For example, if the parent of a male, 75 lb, child (under 13) sees a red indication, the parent knows the child just received AT LEAST an 18G impact. To get the actual reading, the parent can download from the mouth guard, however, the indication is meant to provide instant, visual, indication for the amount of force received (not to make any sort of diagnosis).

By programming in the age, gender, weight, we will start compiling a data base of sports-related impacts across sports, genders, and ages. Taking a 10% (or as indicated with testing) reduction in the required force, thresholds are determined.

Additional variable may also prove effective in predicting/identifying concussive force impacts, such as use of the patients "historical cranial acceleration data" which can be used as an input into the risk function of threshold indication. Meaning, we plan to use our data as an input to determine future risk for specific individuals. Or and in addition to, we can use their reported head-history to make the thresholds less sensitive because they have had head injuries in the past.

Being able to program in the age/gender/weight is essential to one embodiment of the present invention as it allows quantification of the color of the lights. For example, if age/gender/weight were not factors and an athlete received a green LED indication, there would be no way to correlate the color green back to a level of impact force. Did the green indication mean a 20G force impact (likely not dangerous to an adult, but a "red" indication for a child)? Being able to program in the user's biometric data, allows for a level of correlation that provides significance to the color of the LED display.

Further improvements to the present invention include a "high G" accelerometer placed at the intersection of the sagittal and transverse planes of the head (i.e. close to or at dead center), in addition to a low-G accelerometer used to determine when the device is "on". Alternatively, only a High-C accelerometer may be used. The centered placement of the High-G allows the sensor to read as it was intended to and prevents the need for recalibration to help the sensor account for being off center in some way. In embodiments containing at las the Low-G and High-G accelerometers, the Low g accelerometer may have a low threshold, e.g. a max threshold of 5G. If the mouth guard detects anything lower than the Low-G max threshold, the system may stay in a sleep mode to conserve power. However, if the sensor experiences or senses an impact or movement beyond the maximum Low-G setting, e.g. 5G, the device may instantly turn on and also record the impact as captured by the High G accelerometer of the event.

Similarly, the gyroscope is measuring rotation, so there is not the same requirement to have the sensor front and center.

As can be seen in FIGS. 19-23, the LED may be placed in the true center of the transverse plane of the head, but slightly lower on the sagittal plane (i.e. below 'dead center') because the view angle is the best from the middle, but having the LED at true center (or above true center) allows it to be too easily covered by the user's lips. Positioning the LED precisely on this point provides optimum viewing angle, with the lowest opportunity for obstruction.

Mouth guard 900 includes frontal board 901 which may include a motion/force sensor and/or display and/or ambient light sensor. It is preferred that the light display is made at the very bottom front corner to increase display visibility. Alternatively, or in conjunction, the ambient light sensor will be placed toward the front bottom, or even the underside of the front PCB. Display light may also be positioned on underside of frontal PCB.

Left board 902 may be disconnected from frontal board 902, as well as right board 903. Boards 901, 902, and 903, may be connected by a wire, such a sa ribbon wire. The use of hard PCBs has been shown to hold up better than flexible PCBs, however as technology develops, flexible PCBs, including a single long PCB may be used. Gyro sensor 910 may be included. Wire 909 may be used to connect the varied boards. Bite pad 905 may include a pressure sensor to determine the pressure or force on the mouth guard to test if the mouth/jaws are in a closed or clenched position, which information is especially useful during or immediately prior to impact event.

As can be seen in FIGS. 24-26, device 1000 may include ambient light sensor 1001. Hard circuit boards 1010 and 1020 may be placed in the side walls. A hole or cut out or relatively thin layer 1030 may be placed in the front wall to allow ambient light senor to detect ambient light and help determine if mouth is/was closed during an impact event.

Regarding the type of printed circuit board used, even though flexible PCB technology has evolved a great deal and PCBs are able to fit the spatial constraints of a mouth guard, an alternative embodiment utilizes a rigid PCB or set thereof. When flexing a flexible PCB to fit into a mouth guard, and exposing that PCB to impacts (while encased in a mouth guard or other wearable device) the extreme stress and fatigue on the solder points and wiring of the board can cause the flexible PCB to fail. Instead, in this alternative embodiment, two small, rigid PCBs, the battery, and the charging coil are wired together using a ribbon cable(s). This arrangement gives us the flexibility to keep a single, very small, PCB front and center for the high G accelerometer and LED, while moving the other technology (gyro, MCU, blue tooth antenna, etc.) and large components (battery, charging coil) to the sides of the mouth where the additional thickness is not noticed by the user. We positioned our components in a variety of locations and learned that the front of the mouth is extremely sensitive to extra depth of a mouth guard, but the in the molar-area the additional thickness goes completely unnoticed by the user.

Optical (or ambient) light sensor(s) may be included in an alternative embodiment of the present invention. The optical light sensor may read ambient light and is preferably extremely sensitive. Including an optical light sensor would allow determination if a user's mouth was open or closed during the impact This information as to the positon and arrangement of user's jaw upon impact, may help factor in a clenched or open jaw to our measurement and display. The determination of the arraignment of the jaw at impact may be a "Yes/No" with a measurement of "was ambient light detected at time of impact?", or may include gradations of light sensed to determine the amount the jaw was agape. Optical light sensor may also be calibrated depending on the circumstances of the use, e.g. daylight vs. night, indoor, vs. outdoor, etc. The idea being that an impact with light detected was likely harder than measured and displayed, because the mouth guard moved in an open mouth and that movement reduced some of the impact measured by the sensors. Similarly, we could use a strain gauge or pressure gauge. However, those are devices that measure a clenching force and would have to be placed between the teeth, which could be dangerous for users (and are therefore not preferred). The ambient light sensor on the front panel allows a reading without putting tech between the teeth.

The optical light sensor, or pressure gauge, may provide information as to the "relative jaw pressure" that may have been in place at time (or immediately preceding) impact. Relative jaw pressure may include a simple reading of open or closed mouth, but may also include information as to the pressure of the upper and lower jaw forced relative to one another. Such relative jaw pressure may be included along with biometric data to help determine the risk of injury.

We claim:

1. A mouth guard for detecting impacts experienced by a user during an activity, the mouth guard comprising:
    a main body comprising a soft plastic material, the main body being configured to fit into an oral cavity of the user;
    at least one force detector disposed within or coupled to the main body, the at least one force detector being configured to detect force imparted to the user by the impacts;
    a memory device disposed within or coupled to the main body, the memory device storing a first impact threshold and a second impact threshold that is less than the first impact threshold;
    at least one display light disposed within or coupled to the main body; and
    a microcontroller disposed within or coupled to the main body,
    wherein the microcontroller is configured to, during the activity, lower the first impact threshold in response to the at least one force detector detecting an initial impact that exceeds the second impact threshold but not the first impact threshold, and
    wherein the microcontroller is configured to, during the activity, provide an indication using the at least one display light in response to the at least one force detector detecting at least one subsequent impact that exceeds the lowered first impact threshold but does not exceed the first impact threshold.

2. The mouth guard of claim 1, wherein the lowering of the first impact threshold is based in part on at least one of (i) biometric data associated with the user or (ii) a type of impact for the initial impact.

3. The mouth guard of claim 2, wherein the type of impact for the initial impact includes a first type of impact with imparted linear force greater than imparted rotational force, a second type of impact with imparted rotational force greater than imparted linear force, a third type of impact with imparted linear force equal to imparted rotational force, a fourth type of impact originating from a first direction relative to the user, a fifth type of impact originating from a second direction relative to the user that is different than the first direction, or any combination thereof.

4. The mouth guard of claim 1, wherein the at least one force detector is configured to detect linear force imparted to the user and rotational force imparted to the user, and wherein the first impact threshold includes a linear dimension corresponding to a linear force threshold for the linear force imparted to the user, and a rotational dimension corresponding to a rotational force threshold for the rotational force imparted to the user.

5. The mouth guard of claim 4, wherein the linear dimension includes a plurality of linear threshold values and the rotational dimension includes a plurality of rotational threshold values, each of the plurality of linear threshold values corresponding to a distinct one of the plurality of rotational threshold values, such that the linear dimension and the rotational dimension of the first impact threshold form a curve that defines threshold pairs of imparted linear force and imparted rotational force.

6. The mouth guard of claim 4, wherein the lowering of the first impact threshold includes at least one of (i) lowering the linear force threshold or (ii) lowering the rotational force threshold.

7. The mouth guard of claim 4, wherein the lowering of the first impact threshold includes disproportionately lowering the linear force threshold compared to the rotational force threshold, or disproportionately lowering the rotational force threshold compared to the linear force threshold, the disproportionate lowering of either the linear force threshold or the rotational force threshold being based in part on at least one of (i) biometric data of the user or (ii) a type of impact for the initial impact.

8. The mouth guard of claim 4, wherein the second impact threshold includes a linear force threshold and a rotational force threshold.

9. The mouth guard of claim 8, wherein the initial impact exceeds the second impact threshold but not the first impact threshold if the initial impact imparts (i) an amount of linear force that exceeds the linear force threshold of the second impact threshold but not the linear force threshold of the first impact threshold, and (ii) an amount of rotational force that does not exceed the rotational force threshold of the first impact threshold or the rotational force threshold of the second impact threshold.

10. The mouth guard of claim 8, wherein the initial impact exceeds the second impact threshold but not the first impact threshold if the initial impact imparts (i) an amount of linear force that does not exceed the linear force threshold of the first impact threshold or the linear force threshold of the second impact threshold, and (ii) an amount of rotational force that exceeds the rotational force threshold of the second impact threshold but not the rotational force threshold of the first impact threshold.

11. The mouth guard of claim 8, wherein the initial impact exceeds the second impact threshold but not the first impact threshold if the initial impact imparts (i) an amount of linear force that exceeds the linear force threshold of the second impact threshold but not the linear force threshold of the first impact threshold, and (ii) an amount of rotational force that exceeds the rotational force threshold of the second impact threshold but not the rotational force threshold of the first impact threshold.

\* \* \* \* \*